United States Patent
Wysocki et al.

(10) Patent No.: US 9,868,041 B2
(45) Date of Patent: Jan. 16, 2018

(54) INTEGRATED MEDIA JUKEBOX AND PHYSIOLOGIC DATA HANDLING APPLICATION

(71) Applicant: Apple Inc., Cupertino, CA (US)

(72) Inventors: Christopher R. Wysocki, Los Gatos, CA (US); David Heller, San Jose, CA (US); Amandeep Jawa, San Francisco, CA (US); Sandeep Gupta, Fremont, CA (US); Greg Marriott, Honolulu, HI (US); Max Sprauer, San Jose, CA (US); David A. Shayer, Palo Alto, CA (US); John Wesley Archibald, Sunnyvale, CA (US); Shannon E. Wells, Santa Clara, CA (US)

(73) Assignee: Apple, Inc., Cupertino, CA (US)

( * ) Notice: Subject to any disclaimer, the term of this patent is extended or adjusted under 35 U.S.C. 154(b) by 0 days.

(21) Appl. No.: 14/263,813

(22) Filed: Apr. 28, 2014

(65) Prior Publication Data

US 2014/0236945 A1    Aug. 21, 2014

Related U.S. Application Data

(60) Continuation of application No. 13/605,939, filed on Sep. 6, 2012, now abandoned, which is a division of
(Continued)

(51) Int. Cl.
*G06F 3/00* (2006.01)
*G06F 13/12* (2006.01)
(Continued)

(52) U.S. Cl.
CPC ...... *A63B 69/0028* (2013.01); *A63B 71/0686* (2013.01); *G06F 3/002* (2013.01);
(Continued)

(58) Field of Classification Search
CPC .... G06F 3/0601; G06F 9/4411; G06F 13/385; G06F 2003/0692; G06F 3/00;
(Continued)

(56) References Cited

U.S. PATENT DOCUMENTS 3,612,265 A    10/1971    Dickerson
3,807,388 A     4/1974    Orr et al.
(Continued)

FOREIGN PATENT DOCUMENTS

AU    2007268089        12/2007
DE    4334773 A1         4/1994
(Continued)

OTHER PUBLICATIONS

U.S. Appl. No. 10/125,893, filed Apr. 18, 2002, entitled "Power Adapters for Powering and/or Charging Peripheral Devices".
(Continued)

*Primary Examiner* — Farley Abad
*Assistant Examiner* — Henry Yu
(74) *Attorney, Agent, or Firm* — Fletcher Yoder, P.C.

(57) ABSTRACT

A method is provided to operate a computer to interoperate with a portable media player. The method includes processing signals provided from the portable media player to the computer that are indicative of whether an accessory has been connected to the portable media player, to determine whether the accessory has been connected to the portable media player. Based on a determination that the accessory has been connected to the portable media player, physiologic data of a user that was provided to the portable media player from a wireless physiologic data gathering device, is received from the portable media player, into the computer, via the accessory.

19 Claims, 9 Drawing Sheets

Related U.S. Application Data application No. 11/419,737, filed on May 22, 2006, now abandoned.

(51) Int. Cl.
    *A63B 71/00* (2006.01)
    *G10H 7/00* (2006.01)
    *A61B 5/00* (2006.01)
    *A61B 6/04* (2006.01)
    *A63B 69/00* (2006.01)
    *G06Q 50/22* (2012.01)
    *G06F 17/30* (2006.01)
    *A63B 71/06* (2006.01)

(52) U.S. Cl.
    CPC ....... *G06F 17/30053* (2013.01); *G06Q 50/22* (2013.01); *A63B 71/0622* (2013.01); *A63B 2071/0625* (2013.01); *A63B 2225/20* (2013.01); *A63B 2225/50* (2013.01)

(58) Field of Classification Search
    CPC ............... G06F 17/30053; H04L 43/00; H04L 43/0817; A63B 69/0028; A63B 71/0686; A63B 71/0622
    USPC .................. 710/2, 15, 18, 62, 64, 72; 482/8; 84/612, 615; 600/300, 519, 545; 707/102, 104.1
    See application file for complete search history.

(56) References Cited

U.S. PATENT DOCUMENTS

| | | |
|---|---|---|
| 3,918,058 A | 11/1975 | Noyori et al. |
| 3,958,459 A | 5/1976 | Shimomura |
| 3,978,725 A | 9/1976 | Haditke |
| 4,089,057 A | 5/1978 | Eriksson |
| 4,090,216 A | 5/1978 | Constable |
| 4,101,873 A | 7/1978 | Anderson et al. |
| 4,114,450 A | 9/1978 | Shulman et al. |
| 4,195,642 A | 4/1980 | Price et al. |
| 4,210,024 A | 7/1980 | Ishiwatari et al. |
| 4,223,211 A | 9/1980 | Allsen et al. |
| 4,248,244 A | 2/1981 | Charnitski et al. |
| 4,317,126 A | 2/1982 | Gragg, Jr. |
| 4,371,188 A | 2/1983 | Hull |
| 4,371,945 A | 2/1983 | Karr et al. |
| 4,375,674 A | 3/1983 | Thornton |
| 4,386,345 A | 5/1983 | Narveson et al. |
| 4,423,630 A | 1/1984 | Morrison |
| 4,434,801 A | 3/1984 | Jiminez et al. |
| 4,451,849 A | 5/1984 | Fuhrer |
| 4,516,110 A | 5/1985 | Overmyer |
| 4,516,865 A | 5/1985 | Hideo |
| 4,578,769 A | 3/1986 | Frederick |
| 4,589,022 A | 5/1986 | Prince et al. |
| 4,625,733 A | 12/1986 | Saynajakangas |
| 4,649,552 A | 3/1987 | Yukawa |
| 4,694,694 A | 9/1987 | Vlakancic et al. |
| 4,699,379 A | 10/1987 | Chateau et al. |
| 4,703,445 A | 10/1987 | Dassler |
| 4,720,093 A | 1/1988 | Del Mar |
| 4,722,222 A | 2/1988 | Purdy et al. |
| 4,736,312 A | 4/1988 | Dassler et al. |
| 4,745,564 A | 5/1988 | Tennes et al. |
| 4,757,453 A | 7/1988 | Nasiff |
| 4,757,714 A | 7/1988 | Purdy et al. |
| 4,759,219 A | 7/1988 | Cobb et al. |
| 4,763,275 A | 8/1988 | Carlin |
| 4,763,284 A | 8/1988 | Carlin |
| 4,763,287 A | 8/1988 | Gerhaeuser et al. |
| 4,771,394 A | 9/1988 | Cavanagh |
| 4,774,679 A | 9/1988 | Carlin |
| 4,775,948 A | 10/1988 | Dial et al. |
| 4,780,837 A | 10/1988 | Namekawa |
| 4,821,218 A | 4/1989 | Potsch |
| 4,822,042 A | 4/1989 | Landsman |
| 4,824,107 A | 4/1989 | French |
| 4,829,812 A | 5/1989 | Parks et al. |
| 4,830,021 A | 5/1989 | Thornton |
| 4,862,394 A | 8/1989 | Thompson et al. |
| 4,862,395 A | 8/1989 | Fey et al. |
| 4,873,867 A | 10/1989 | McPherson et al. |
| 4,876,500 A | 10/1989 | Wu |
| 4,883,271 A | 11/1989 | French |
| 4,903,212 A | 2/1990 | Yokouchi et al. |
| 4,908,523 A | 3/1990 | Snowden et al. |
| 4,928,307 A | 5/1990 | Lynn |
| 4,935,887 A | 6/1990 | Abdalah et al. |
| 4,951,171 A | 8/1990 | Tran et al. |
| 4,955,980 A | 9/1990 | Masuo |
| 5,033,013 A | 7/1991 | Kato et al. |
| 5,036,467 A | 7/1991 | Blackburn et al. |
| 5,056,783 A | 10/1991 | Matcovich et al. |
| 5,067,081 A | 11/1991 | Person |
| 5,088,836 A | 2/1992 | Yamada et al. |
| 5,117,444 A | 5/1992 | Sutton et al. |
| 5,144,226 A | 9/1992 | Rapp |
| 5,148,002 A | 9/1992 | Kuo et al. |
| 5,150,310 A | 9/1992 | Greenspun et al. |
| 5,162,828 A | 11/1992 | Furness et al. |
| 5,164,831 A | 11/1992 | Kuchta et al. |
| 5,181,181 A | 1/1993 | Glynn |
| 5,200,827 A | 4/1993 | Hanson et al. |
| 5,243,993 A | 9/1993 | Alexander et al. |
| 5,258,927 A | 11/1993 | Havriluk et al. |
| 5,295,085 A | 3/1994 | Hoffacker |
| 5,316,249 A | 5/1994 | Anderson |
| 5,324,038 A | 6/1994 | Sasser |
| 5,335,664 A | 8/1994 | Nagashima |
| 5,339,699 A | 8/1994 | Carignan |
| 5,341,350 A | 8/1994 | Frank et al. |
| 5,343,445 A | 8/1994 | Cherdak |
| 5,348,519 A | 9/1994 | Prince et al. |
| 5,382,972 A | 1/1995 | Kannes |
| 5,396,429 A | 3/1995 | Hanchett |
| 5,406,305 A | 4/1995 | Shimomura et al. |
| 5,420,828 A | 5/1995 | Geiger |
| 5,426,595 A | 6/1995 | Picard |
| 5,436,838 A | 7/1995 | Miyamori |
| 5,446,775 A | 8/1995 | Wright et al. |
| 5,450,329 A | 9/1995 | Tanner |
| 5,452,269 A | 9/1995 | Cherdak |
| 5,471,405 A | 11/1995 | Marsh |
| 5,475,725 A | 12/1995 | Nakamura |
| 5,476,427 A | 12/1995 | Fujima |
| 5,478,006 A | 12/1995 | Taguchi |
| 5,485,402 A | 1/1996 | Smith et al. |
| 5,486,815 A | 1/1996 | Wagner |
| 5,509,082 A | 4/1996 | Toyama et al. |
| 5,513,854 A | 5/1996 | Daver |
| 5,524,637 A | 6/1996 | Erickson |
| 5,526,326 A | 6/1996 | Fekete et al. |
| 5,528,228 A | 6/1996 | Wilk |
| 5,539,336 A | 7/1996 | Nguyen et al. |
| 5,541,604 A | 7/1996 | Meier |
| 5,546,307 A | 8/1996 | Mazur et al. |
| 5,546,974 A | 8/1996 | Bireley |
| 5,557,541 A | 9/1996 | Schulhof et al. |
| 5,559,945 A | 9/1996 | Beaudet et al. |
| 5,564,698 A | 10/1996 | Honey et al. |
| 5,574,669 A | 11/1996 | Marshall |
| 5,583,776 A | 12/1996 | Levi et al. |
| 5,583,993 A | 12/1996 | Foster et al. |
| 5,590,908 A | 1/1997 | Carr |
| 5,592,401 A | 1/1997 | Kramer |
| 5,605,336 A | 2/1997 | Gaoiran et al. |
| 5,608,698 A | 3/1997 | Yamanoi et al. |
| 5,615,132 A | 3/1997 | Horton et al. |
| 5,616,876 A | 4/1997 | Cluts |
| 5,617,084 A | 4/1997 | Sears |
| 5,617,386 A | 4/1997 | Choi |
| 5,618,995 A | 4/1997 | Otto et al. |
| 5,627,548 A | 5/1997 | Woo et al. |

(56) References Cited

U.S. PATENT DOCUMENTS

| | | |
|---|---|---|
| 5,629,131 A | 5/1997 | De Keyzer et al. |
| 5,633,070 A | 5/1997 | Murayama et al. |
| 5,636,146 A | 6/1997 | Flentov et al. |
| 5,646,857 A | 7/1997 | McBurney et al. |
| 5,670,985 A | 9/1997 | Cappels, Sr. et al. |
| 5,671,010 A | 9/1997 | Shimbo et al. |
| 5,671,162 A | 9/1997 | Werbin |
| 5,673,691 A | 10/1997 | Abrams et al. |
| 5,680,102 A | 10/1997 | Xydis |
| 5,684,513 A | 11/1997 | Decker |
| 5,688,183 A | 11/1997 | Sabatino et al. |
| 5,690,119 A | 11/1997 | Rytky et al. |
| 5,690,591 A | 11/1997 | Kenmochi et al. |
| 5,690,773 A | 11/1997 | Fidalgo et al. |
| 5,694,340 A | 12/1997 | Kim |
| 5,701,257 A | 12/1997 | Miura et al. |
| 5,710,922 A | 1/1998 | Alley et al. |
| 5,712,638 A | 1/1998 | Issa |
| 5,712,949 A | 1/1998 | Kato et al. |
| 5,720,200 A | 2/1998 | Anderson et al. |
| 5,721,539 A | 2/1998 | Goetzi |
| 5,721,949 A | 2/1998 | Smith et al. |
| 5,723,786 A | 3/1998 | Klapman |
| 5,724,265 A | 3/1998 | Hutchings |
| 5,726,672 A | 3/1998 | Hernandez et al. |
| 5,734,337 A | 3/1998 | Kupersmit |
| 5,738,104 A | 4/1998 | Lo et al. |
| 5,739,451 A | 4/1998 | Winksy et al. |
| 5,740,143 A | 4/1998 | Suetomi |
| 5,743,269 A | 4/1998 | Okigami et al. |
| 5,745,037 A | 4/1998 | Guthrie et al. |
| 5,749,615 A | 5/1998 | Itson |
| 5,761,096 A | 6/1998 | Zakutin |
| 5,771,485 A | 6/1998 | Echigo |
| 5,779,576 A | 7/1998 | Smith, III et al. |
| 5,781,155 A | 7/1998 | Woo et al. |
| 5,790,477 A | 8/1998 | Hauke |
| 5,794,164 A | 8/1998 | Beckert et al. |
| 5,797,089 A | 8/1998 | Nguyen |
| 5,807,284 A | 9/1998 | Foxlin |
| 5,812,056 A | 9/1998 | Law |
| 5,812,870 A | 9/1998 | Kikinis et al. |
| 5,815,225 A | 9/1998 | Nelson |
| 5,822,288 A | 10/1998 | Shinada |
| 5,835,721 A | 11/1998 | Donahue et al. |
| 5,835,732 A | 11/1998 | Kikinis et al. |
| 5,862,803 A | 1/1999 | Besson et al. |
| 5,864,868 A | 1/1999 | Contois |
| 5,870,710 A | 2/1999 | Ozawa et al. |
| 5,886,739 A | 3/1999 | Winningstad |
| 5,891,042 A | 4/1999 | Sham et al. |
| 5,895,073 A | 4/1999 | Moore |
| 5,897,457 A | 4/1999 | Mackovjak |
| 5,899,963 A | 5/1999 | Hutchings |
| 5,901,303 A | 5/1999 | Chew |
| 5,905,460 A | 5/1999 | Odagiri et al. |
| 5,914,941 A | 6/1999 | Janky |
| 5,918,281 A | 6/1999 | Nabulsi |
| 5,918,303 A | 6/1999 | Yamaura et al. |
| 5,920,728 A | 7/1999 | Hallowell et al. |
| 5,923,757 A | 7/1999 | Hocker et al. |
| 5,925,001 A | 7/1999 | Hoyt et al. |
| 5,929,335 A | 7/1999 | Carter |
| 5,930,741 A | 7/1999 | Kramer |
| 5,936,523 A | 8/1999 | West |
| 5,946,643 A | 8/1999 | Zakutin |
| 5,947,917 A | 9/1999 | Carte et al. |
| 5,952,992 A | 9/1999 | Helms |
| 5,955,667 A | 9/1999 | Fyfe |
| 5,956,651 A | 9/1999 | Willkie et al. |
| 5,959,568 A | 9/1999 | Wooley |
| 5,960,380 A | 9/1999 | Flentov et al. |
| 5,963,523 A | 10/1999 | Kayama et al. |
| 5,963,891 A | 10/1999 | Walker |
| 5,963,916 A | 10/1999 | Kaplan |
| 5,974,333 A | 10/1999 | Chen |
| 5,976,083 A | 11/1999 | Richardson et al. |
| 5,977,877 A | 11/1999 | McCulloch et al. |
| 5,978,972 A | 11/1999 | Stewart et al. |
| 5,983,073 A | 11/1999 | Ditzik |
| 5,984,842 A | 11/1999 | Chu |
| 5,991,640 A | 11/1999 | Lilja et al. |
| 6,002,982 A | 12/1999 | Fry |
| 6,006,274 A | 12/1999 | Hawkins et al. |
| 6,007,228 A | 12/1999 | Agarwal et al. |
| 6,009,237 A | 12/1999 | Hirabayashi et al. |
| 6,009,629 A | 1/2000 | Gnepf et al. |
| 6,011,491 A | 1/2000 | Goetzi |
| 6,011,585 A | 1/2000 | Anderson |
| 6,013,007 A | 1/2000 | Root et al. |
| 6,018,677 A | 1/2000 | Vidrine et al. |
| 6,018,705 A | 1/2000 | Gaudet et al. |
| 6,020,851 A | 2/2000 | Busack |
| 6,028,617 A | 2/2000 | Helmsderfer |
| 6,028,625 A | 2/2000 | Cannon |
| 6,028,627 A | 2/2000 | Helmsderfer |
| 6,032,084 A | 2/2000 | Anderson et al. |
| 6,032,108 A | 2/2000 | Seiple et al. |
| 6,032,530 A | 3/2000 | Hock |
| 6,038,199 A | 3/2000 | Pawlowski et al. |
| 6,041,023 A | 3/2000 | Lakhansingh |
| 6,043,747 A | 3/2000 | Altenhofen |
| 6,045,364 A | 4/2000 | Dugan et al. |
| 6,047,054 A | 4/2000 | Bayless et al. |
| 6,052,654 A | 4/2000 | Gaudet et al. |
| 6,057,756 A | 5/2000 | Engellenner |
| 6,059,576 A | 5/2000 | Brann |
| 6,061,306 A | 5/2000 | Buchheim |
| 6,073,086 A | 6/2000 | Marinelli |
| 6,074,271 A | 6/2000 | Derrah |
| 6,075,443 A | 6/2000 | Schepps et al. |
| 6,091,342 A | 7/2000 | Janesch et al. |
| 6,108,426 A | 8/2000 | Stortz |
| 6,111,541 A | 8/2000 | Karmel |
| 6,111,571 A | 8/2000 | Summers |
| 6,122,340 A | 9/2000 | Darley et al. |
| 6,122,959 A | 9/2000 | Hoshal et al. |
| 6,122,960 A | 9/2000 | Hutchings |
| 6,125,686 A | 10/2000 | Haan |
| 6,127,931 A | 10/2000 | Mohr |
| 6,135,951 A | 10/2000 | Richardson |
| 6,145,389 A | 11/2000 | Ebeling et al. |
| 6,148,271 A | 11/2000 | Marinelli |
| 6,151,647 A | 11/2000 | Sarat |
| 6,157,898 A | 12/2000 | Marinelli |
| 6,160,254 A | 12/2000 | Zimmerman et al. |
| 6,160,551 A | 12/2000 | Naughton et al. |
| 6,161,944 A | 12/2000 | Leman |
| 6,163,021 A | 12/2000 | Mickelson |
| 6,167,356 A | 12/2000 | Squadron et al. |
| 6,172,948 B1 | 1/2001 | Keller et al. |
| 6,177,950 B1 | 1/2001 | Robb |
| 6,179,432 B1 | 1/2001 | Zhang et al. |
| 6,183,425 B1 | 2/2001 | Whalen et al. |
| 6,185,491 B1 | 2/2001 | Gray et al. |
| 6,191,939 B1 | 2/2001 | Burnett |
| 6,192,340 B1 | 2/2001 | Abecassis |
| 6,196,932 B1 | 3/2001 | Marsh et al. |
| 6,204,813 B1 | 3/2001 | Wadell et al. |
| 6,208,044 B1 | 3/2001 | Viswanadham et al. |
| 6,216,131 B1 | 4/2001 | Liu et al. |
| 6,217,183 B1 | 4/2001 | Shipman |
| 6,226,622 B1 | 5/2001 | Dabbiere |
| 6,230,322 B1 | 5/2001 | Saib et al. |
| 6,232,539 B1 | 5/2001 | Looney et al. |
| 6,238,338 B1 | 5/2001 | DeLuca et al. |
| 6,245,002 B1 | 6/2001 | Belikov |
| 6,247,130 B1 | 6/2001 | Fritsch |
| 6,248,946 B1 | 6/2001 | Dwek |
| 6,249,487 B1 | 6/2001 | Yano et al. |
| 6,254,513 B1 | 7/2001 | Takenaka et al. |
| 6,255,961 B1 | 7/2001 | Van Ryzin et al. |
| 6,259,892 B1 | 7/2001 | Helferich |
| 6,263,279 B1 | 7/2001 | Bianco et al. |

(56) References Cited

U.S. PATENT DOCUMENTS

| | | |
|---|---|---|
| 6,266,623 B1 | 7/2001 | Vock et al. |
| 6,278,447 B1 | 8/2001 | Anderson |
| 6,282,464 B1 | 8/2001 | Obradovich |
| 6,295,541 B1 | 9/2001 | Bodnar et al. |
| 6,298,314 B1 | 10/2001 | Blackadar et al. |
| 6,305,221 B1 | 10/2001 | Hutchings |
| 6,314,094 B1 | 11/2001 | Boys |
| 6,314,326 B1 | 11/2001 | Fuchu |
| 6,332,175 B1 | 12/2001 | Birrell et al. |
| 6,336,365 B1 | 1/2002 | Blackadar et al. |
| 6,336,727 B1 | 1/2002 | Kim |
| 6,338,044 B1 | 1/2002 | Cook et al. |
| 6,339,706 B1 | 1/2002 | Tillgren et al. |
| 6,341,316 B1 | 1/2002 | Kloba et al. |
| 6,353,637 B1 | 3/2002 | Mansour et al. |
| 6,356,856 B1 | 3/2002 | Damen et al. |
| 6,357,147 B1 | 3/2002 | Darley et al. |
| 6,360,597 B1 | 3/2002 | Hubbard, Jr. |
| 6,377,530 B1 | 4/2002 | Burrows |
| 6,377,825 B1 | 4/2002 | Kennedy et al. |
| 6,380,597 B1 | 4/2002 | Gudesen et al. |
| 6,385,473 B1 | 5/2002 | Haines et al. |
| 6,396,164 B1 | 5/2002 | Barnea et al. |
| 6,401,085 B1 | 6/2002 | Gershman et al. |
| 6,407,750 B1 | 6/2002 | Gioscia et al. |
| 6,408,332 B1 | 6/2002 | Matsumoto et al. |
| 6,418,330 B1 | 7/2002 | Lee |
| 6,421,305 B1 | 7/2002 | Gioscia et al. |
| 6,436,052 B1 | 8/2002 | Nikolic et al. |
| 6,441,747 B1 | 8/2002 | Khair et al. |
| 6,452,610 B1 | 9/2002 | Reinhardt et al. |
| 6,456,261 B1 | 9/2002 | Zhang |
| 6,459,881 B1 | 10/2002 | Hoder et al. |
| 6,463,385 B1 | 10/2002 | Fry |
| 6,467,924 B2 | 10/2002 | Shipman |
| 6,473,630 B1 | 10/2002 | Baranowski et al. |
| 6,487,663 B1 | 11/2002 | Jaisimha et al. |
| 6,493,652 B1 | 12/2002 | Ohlenbusch et al. |
| 6,496,692 B1 | 12/2002 | Shanahan |
| 6,498,994 B2 | 12/2002 | Vock et al. |
| 6,501,393 B1 | 12/2002 | Richards et al. |
| 6,504,483 B1 | 1/2003 | Richards et al. |
| 6,510,210 B1 | 1/2003 | Baughan |
| 6,510,325 B1 | 1/2003 | Mack, II et al. |
| 6,516,284 B2 | 2/2003 | Flentov et al. |
| 6,516,466 B1 | 2/2003 | Jackson |
| 6,526,335 B1 | 2/2003 | Treyz et al. |
| 6,527,711 B1 | 3/2003 | Stivoric |
| 6,529,131 B2 | 3/2003 | Wentworth |
| 6,531,982 B1 | 3/2003 | White et al. |
| 6,535,914 B1 | 3/2003 | Pearson et al. |
| 6,535,983 B1 | 3/2003 | McCormack et al. |
| 6,536,139 B2 | 3/2003 | Darley et al. |
| 6,539,336 B1 | 3/2003 | Vock et al. |
| 6,549,497 B2 | 4/2003 | Miyamoto et al. |
| 6,559,773 B1 | 5/2003 | Berry |
| 6,560,903 B1 | 5/2003 | Darley |
| 6,563,417 B1 | 5/2003 | Shaw |
| 6,570,526 B1 | 5/2003 | Noller et al. |
| 6,582,342 B2 | 6/2003 | Kaufman |
| 6,587,127 B1 | 7/2003 | Leeke et al. |
| 6,587,403 B1 | 7/2003 | Keller et al. |
| 6,587,404 B1 | 7/2003 | Keller et al. |
| 6,595,929 B2 | 7/2003 | Stivoric |
| 6,600,418 B2 | 7/2003 | Sainati et al. |
| 6,605,038 B1 | 8/2003 | Teller et al. |
| 6,609,105 B2 | 8/2003 | Van Zoest et al. |
| 6,611,782 B1 | 8/2003 | Wooster |
| 6,611,789 B1 | 8/2003 | Darley |
| 6,617,962 B1 | 9/2003 | Horwitz et al. |
| 6,619,835 B2 | 9/2003 | Kita |
| 6,621,768 B1 | 9/2003 | Keller et al. |
| 6,623,427 B2 | 9/2003 | Mandigo |
| 6,633,743 B1 | 10/2003 | Berlinsky |
| 6,633,932 B1 | 10/2003 | Bork et al. |
| 6,643,608 B1 | 11/2003 | Hershey et al. |
| 6,658,247 B1 | 12/2003 | Saito |
| 6,671,567 B1 | 12/2003 | Dwyer et al. |
| 6,675,233 B1 | 1/2004 | Du et al. |
| 6,694,200 B1 | 2/2004 | Naim |
| 6,714,121 B1 | 3/2004 | Moore |
| 6,716,139 B1 | 4/2004 | Hosseinzadeh-Dolkhani et al. |
| 6,728,531 B1 | 4/2004 | Lee et al. |
| 6,731,312 B2 | 5/2004 | Robbin |
| 6,735,630 B1 | 5/2004 | Gelvin et al. |
| 6,745,411 B1 | 6/2004 | Kjonaas |
| 6,748,902 B1 | 6/2004 | Boesch et al. |
| 6,760,536 B1 | 7/2004 | Amir et al. |
| 6,762,741 B2 | 7/2004 | Weindorf |
| 6,772,212 B1 | 8/2004 | Lau et al. |
| 6,772,331 B1 | 8/2004 | Hind et al. |
| 6,790,178 B1 | 9/2004 | Mault et al. |
| 6,793,607 B2 | 9/2004 | Neil |
| 6,794,566 B2 | 9/2004 | Pachet |
| 6,799,226 B1 | 9/2004 | Robbin et al. |
| 6,801,964 B1 | 10/2004 | Mahdavi |
| 6,813,586 B1 | 11/2004 | Vock et al. |
| 6,823,225 B1 | 11/2004 | Sass |
| 6,825,777 B2 | 11/2004 | Vock et al. |
| 6,837,827 B1 * | 1/2005 | Lee .................. A63B 24/0021 482/3 |
| 6,845,398 B1 | 1/2005 | Galensky et al. |
| 6,856,934 B2 | 2/2005 | Vock et al. |
| 6,870,529 B1 | 3/2005 | Davis |
| 6,871,063 B1 | 3/2005 | Schiffer |
| 6,876,947 B1 | 4/2005 | Darley et al. |
| 6,882,955 B1 | 4/2005 | Ohlenbusch et al. |
| 6,883,694 B2 | 4/2005 | Abelow |
| 6,885,971 B2 | 4/2005 | Vock et al. |
| 6,898,550 B1 | 5/2005 | Blackadar et al. |
| 6,900,732 B2 | 5/2005 | Richards |
| 6,901,067 B1 | 5/2005 | Kalavade |
| 6,907,112 B1 | 6/2005 | Guedalia et al. |
| 6,911,971 B2 | 6/2005 | Suzuki et al. |
| 6,914,551 B2 | 7/2005 | Vidal |
| 6,915,272 B1 | 7/2005 | Zilliacus et al. |
| 6,917,923 B1 | 7/2005 | Dimenstein |
| 6,918,677 B2 | 7/2005 | Shipman |
| 6,934,812 B1 | 8/2005 | Robbin et al. |
| 6,950,087 B2 | 9/2005 | Knox et al. |
| 6,959,259 B2 | 10/2005 | Vock et al. |
| 9,154,554 B2 | 10/2005 | Ananny |
| 7,009,517 B2 | 3/2006 | Wood |
| 7,030,735 B2 | 4/2006 | Chen |
| 7,042,360 B2 | 5/2006 | Light et al. |
| 7,046,230 B2 | 5/2006 | Zadesky |
| 7,054,784 B2 | 5/2006 | Flentov et al. |
| 7,062,225 B2 | 6/2006 | White |
| 7,064,669 B2 | 6/2006 | Light et al. |
| 7,065,342 B1 | 6/2006 | Rolf |
| 7,072,789 B2 | 7/2006 | Vock et al. |
| 7,084,856 B2 | 8/2006 | Huppi |
| 7,084,921 B1 | 8/2006 | Ogawa |
| 7,092,846 B2 | 8/2006 | Vock et al. |
| 7,120,462 B2 | 10/2006 | Kumar |
| 7,123,936 B1 | 10/2006 | Rydbeck et al. |
| 7,146,437 B2 | 12/2006 | Robbin et al. |
| 7,149,543 B2 | 12/2006 | Kumar |
| 7,158,912 B2 | 1/2007 | Vock |
| 7,162,392 B2 | 1/2007 | Vock |
| 7,171,331 B2 | 1/2007 | Vock et al. |
| 7,174,130 B2 | 2/2007 | Kurisko et al. |
| 7,174,277 B2 | 2/2007 | Vock et al. |
| 7,187,947 B1 | 3/2007 | White et al. |
| 7,200,517 B2 | 4/2007 | Darley et al. |
| 7,234,026 B2 | 6/2007 | Robbin et al. |
| 7,251,454 B2 | 7/2007 | White |
| 7,254,516 B2 | 8/2007 | Case et al. |
| 7,278,966 B2 | 10/2007 | Hjelt et al. |
| 7,292,588 B2 | 11/2007 | Milley et al. |
| 7,292,867 B2 | 11/2007 | Werner et al. |
| 7,296,107 B2 | 11/2007 | Lunsford et al. |
| 7,321,783 B2 | 1/2008 | Kim |
| 7,324,833 B2 | 1/2008 | White et al. |

(56) References Cited

U.S. PATENT DOCUMENTS

| | | |
|---|---|---|
| 7,339,993 B1 | 3/2008 | Brooks et al. |
| 7,353,136 B2 | 4/2008 | Vock |
| 7,353,137 B2 | 4/2008 | Vock |
| 7,353,139 B1 | 4/2008 | Burrell et al. |
| 7,386,401 B2 | 6/2008 | Vock |
| 7,440,772 B2 | 10/2008 | White et al. |
| 7,444,353 B1 | 10/2008 | Chen et al. |
| 7,450,084 B2 | 11/2008 | Fuller et al. |
| 7,451,056 B2 | 11/2008 | Flentov |
| 7,454,002 B1 | 11/2008 | Gardner et al. |
| 7,486,926 B2 | 2/2009 | White et al. |
| 7,512,515 B2 | 3/2009 | Vock |
| 7,519,327 B2 | 4/2009 | White |
| 7,559,877 B2 | 7/2009 | Parks et al. |
| 7,600,227 B2 | 10/2009 | Brockway et al. |
| 7,634,228 B2 | 12/2009 | White et al. |
| 7,647,129 B1 | 1/2010 | Griffin, Jr. |
| 7,653,928 B2 | 1/2010 | Almstrand et al. |
| 1,685,210 A1 | 3/2010 | Plastina et al. |
| 7,670,263 B2 | 3/2010 | Ellis et al. |
| 7,673,238 B2 | 3/2010 | Oliver |
| 7,683,252 B2 | 3/2010 | Girish |
| 7,698,101 B2 | 4/2010 | Alten |
| 7,711,883 B2 | 5/2010 | Son |
| 7,778,595 B2 | 8/2010 | White et al. |
| 7,783,065 B2 | 8/2010 | Navid |
| 8,099,258 B2 | 1/2012 | Alten |
| 8,482,488 B2 | 7/2013 | Jannard |
| 9,137,309 B2 | 9/2015 | Ananny |
| 2001/0022828 A1 | 9/2001 | Pyles |
| 2001/0029192 A1 | 10/2001 | Oh |
| 2001/0033244 A1 | 10/2001 | Harris et al. |
| 2001/0041021 A1 | 11/2001 | Boyle et al. |
| 2001/0042107 A1 | 11/2001 | Palm |
| 2001/0049890 A1 | 12/2001 | Hirsch et al. |
| 2002/0002413 A1 | 1/2002 | Tokue |
| 2002/0010759 A1 | 1/2002 | Hitson et al. |
| 2002/0013784 A1 | 1/2002 | Swanson |
| 2002/0015362 A1 | 2/2002 | Cowgill et al. |
| 2002/0022551 A1* | 2/2002 | Watterson et al. ........... 482/8 |
| 2002/0032911 A1 | 3/2002 | Tanaka et al. |
| 2002/0045961 A1 | 4/2002 | Gibbs et al. |
| 2002/0046084 A1 | 4/2002 | Steele et al. |
| 2002/0046315 A1 | 4/2002 | Miller et al. |
| 2002/0055934 A1 | 5/2002 | Lipscomb et al. |
| 2002/0077784 A1 | 6/2002 | Vock et al. |
| 2002/0090912 A1 | 7/2002 | Cannon et al. |
| 2002/0116082 A1 | 8/2002 | Gudorf |
| 2002/0144024 A1 | 10/2002 | Kumpf et al. |
| 2002/0152045 A1 | 10/2002 | Dowling et al. |
| 2002/0156833 A1 | 10/2002 | Maurya |
| 2002/0161865 A1 | 10/2002 | Nguyen |
| 2002/0164973 A1 | 11/2002 | Janik et al. |
| 2002/0173273 A1 | 11/2002 | Spurgat et al. |
| 2002/0189426 A1 | 12/2002 | Hirade et al. |
| 2003/0016844 A1 | 1/2003 | Numaoka |
| 2003/0037254 A1 | 2/2003 | Fischer et al. |
| 2003/0046434 A1 | 3/2003 | Flanagin et al. |
| 2003/0060728 A1 | 3/2003 | Mandigo |
| 2003/0065805 A1 | 4/2003 | Barnes |
| 2003/0074457 A1 | 4/2003 | Kluth |
| 2003/0076301 A1 | 4/2003 | Tsuk et al. |
| 2003/0079038 A1 | 4/2003 | Robbin et al. |
| 2003/0095096 A1 | 5/2003 | Robbin et al. |
| 2003/0097379 A1 | 5/2003 | Ireton |
| 2003/0097878 A1 | 5/2003 | Farringdon et al. |
| 2003/0110297 A1 | 6/2003 | Tabatabai et al. |
| 2003/0133694 A1 | 7/2003 | Yeo |
| 2003/0149875 A1 | 8/2003 | Hosaka |
| 2003/0163287 A1 | 8/2003 | Vock et al. |
| 2003/0167318 A1 | 9/2003 | Robbin et al. |
| 2003/0208113 A1 | 11/2003 | Mault et al. |
| 2003/0215102 A1 | 11/2003 | Marlowe |
| 2003/0229490 A1 | 12/2003 | Etter |
| 2004/0001395 A1 | 1/2004 | Keller et al. |
| 2004/0001396 A1 | 1/2004 | Keller et al. |
| 2004/0012556 A1 | 1/2004 | Yong et al. |
| 2004/0055446 A1 | 3/2004 | Robbin et al. |
| 2004/0069122 A1 | 4/2004 | Wilson |
| 2004/0076086 A1 | 4/2004 | Keller et al. |
| 2004/0086120 A1 | 5/2004 | Akins, III et al. |
| 2004/0094018 A1 | 5/2004 | Ueshima et al. |
| 2004/0104845 A1 | 6/2004 | McCarthy |
| 2004/0139233 A1 | 7/2004 | Kellerman et al. |
| 2004/0151327 A1 | 8/2004 | Marlow |
| 2004/0198436 A1 | 10/2004 | Alden |
| 2004/0224638 A1 | 11/2004 | Fadell et al. |
| 2004/0253983 A1 | 12/2004 | Vanhatalo et al. |
| 2004/0267825 A1 | 12/2004 | Novak et al. |
| 2005/0015254 A1 | 1/2005 | Beaman |
| 2005/0027910 A1 | 2/2005 | Barrett, Jr. et al. |
| 2005/0080566 A1 | 4/2005 | Vock et al. |
| 2005/0088275 A1 | 4/2005 | Valoteau et al. |
| 2005/0152294 A1 | 7/2005 | Yu et al. |
| 2005/0166153 A1 | 7/2005 | Eytchison et al. |
| 2005/0172311 A1 | 8/2005 | Hjelt et al. |
| 2005/0177929 A1 | 8/2005 | Greenwald et al. |
| 2005/0245839 A1 | 11/2005 | Stivoric et al. |
| 2005/0262557 A1 | 11/2005 | Fellenstein et al. |
| 2005/0266798 A1 | 12/2005 | Moloney et al. |
| 2005/0266961 A1 | 12/2005 | Shum et al. |
| 2005/0275541 A1 | 12/2005 | Sengupta et al. |
| 2006/0013414 A1 | 1/2006 | Shih |
| 2006/0028845 A1* | 2/2006 | Lin .................. G02B 6/0063 |
| | | 362/623 |
| 2006/0068760 A1 | 3/2006 | Hameed et al. |
| 2006/0094402 A1 | 5/2006 | Kim |
| 2006/0097847 A1 | 5/2006 | Bervoets et al. |
| 2006/0123138 A1 | 6/2006 | Perdomo et al. |
| 2006/0132382 A1 | 6/2006 | Jannard |
| 2006/0135064 A1 | 6/2006 | Cho et al. |
| 2006/0143455 A1 | 6/2006 | Gitzinger |
| 2006/0152377 A1 | 7/2006 | Beebe et al. |
| 2006/0169125 A1* | 8/2006 | Ashkenazi et al. ............. 84/612 |
| 2006/0190577 A1 | 8/2006 | Yamada |
| 2006/0218294 A1 | 9/2006 | Rosenberg |
| 2006/0221788 A1 | 10/2006 | Lindahl et al. |
| 2006/0254409 A1 | 11/2006 | Withop |
| 2006/0265503 A1 | 11/2006 | Jones et al. |
| 2006/0265661 A1 | 11/2006 | Ball |
| 2007/0011919 A1 | 1/2007 | Case, Jr. |
| 2007/0021269 A1 | 1/2007 | Shum |
| 2007/0025194 A1* | 2/2007 | Morse .................. G11B 27/034 |
| | | 369/30.1 |
| 2007/0028009 A1 | 2/2007 | Robbin et al. |
| 2007/0032195 A1 | 2/2007 | Kurisko et al. |
| 2007/0113726 A1* | 5/2007 | Oliver et al. .................... 84/615 |
| 2007/0118043 A1 | 5/2007 | Oliver |
| 2007/0124679 A1 | 5/2007 | Jeong et al. |
| 2007/0168388 A1* | 7/2007 | Plastina .............. G11B 27/034 |
| 2007/0208771 A1 | 9/2007 | Platt |
| 2007/0260483 A1* | 11/2007 | Nurmela ............ A61B 5/0022 |
| | | 705/2 |
| 2007/0270663 A1 | 11/2007 | Ng |
| 2007/0271116 A1 | 11/2007 | Wysocki et al. |
| 2008/0016537 A1 | 1/2008 | Little et al. |
| 2008/0046948 A1 | 2/2008 | Verosub |
| 2008/0125288 A1 | 5/2008 | Case |
| 2012/0331105 A1 | 12/2012 | Wysocki et al. |

FOREIGN PATENT DOCUMENTS

| | | | |
|---|---|---|---|
| DE | 4445023 | A1 | 6/1996 |
| DE | 10325805 | | 1/2005 |
| EP | 0127139 | A1 | 5/1984 |
| EP | 0336782 | A2 | 10/1989 |
| EP | 0578604 | | 1/1994 |
| EP | 0744839 | B1 | 11/1996 |
| EP | 0757437 | A2 | 2/1997 |
| EP | 0863469 | | 9/1998 |
| EP | 0898378 | A2 | 2/1999 |
| EP | 0917077 | | 5/1999 |
| EP | 0917893 | B1 | 5/1999 |
| EP | 0918408 | A2 | 5/1999 |

(56) References Cited

FOREIGN PATENT DOCUMENTS

| | | |
|---|---|---|
| EP | 0982732 A1 | 3/2000 |
| EP | 1007975 | 6/2000 |
| EP | 1028425 | 8/2000 |
| EP | 1028426 A2 | 8/2000 |
| EP | 1076302 | 2/2001 |
| EP | 1289197 A1 | 3/2003 |
| EP | 1455477 A2 | 9/2004 |
| EP | 1536612 | 6/2005 |
| EP | 1566948 | 8/2005 |
| EP | 1796265 | 6/2007 |
| EP | 2036311 | 3/2009 |
| GB | 1567238 A | 5/1980 |
| GB | 2137363 A | 10/1984 |
| GB | 2384399 A | 7/2003 |
| JP | 59023610 A | 2/1984 |
| JP | 03152469 A | 6/1991 |
| JP | H8-6875 | 1/1996 |
| JP | 1098512 | 4/1998 |
| JP | 11164058 | 6/1999 |
| JP | 11242686 | 9/1999 |
| JP | 11288558 | 10/1999 |
| JP | 11317061 | 11/1999 |
| JP | 2000122044 | 4/2000 |
| JP | 2000224099 A | 8/2000 |
| JP | 2000299834 A | 10/2000 |
| JP | 2001312338 A | 11/2001 |
| JP | 2001321202 A | 11/2001 |
| JP | 2002076977 A | 3/2002 |
| JP | 2002101908 | 4/2002 |
| KR | 1999-0073234 | 10/1999 |
| WO | 0133569 A1 | 6/1995 |
| WO | 9516950 A1 | 6/1995 |
| WO | WO9817032 | 4/1998 |
| WO | 9806466 | 12/1998 |
| WO | 9854581 | 12/1998 |
| WO | WO9854581 | 12/1998 |
| WO | 0022820 A1 | 4/2000 |
| WO | WO200051259 | 8/2000 |
| WO | 0054462 A1 | 9/2000 |
| WO | 0070523 A1 | 11/2000 |
| WO | 0078170 | 12/2000 |
| WO | 0101706 A1 | 4/2001 |
| WO | 0165413 A1 | 9/2001 |
| WO | 0167753 A1 | 9/2001 |
| WO | 0225610 A1 | 3/2002 |
| WO | 02093272 A1 | 11/2002 |
| WO | WO2003036647 | 5/2003 |
| WO | 03023786 A2 | 8/2003 |
| WO | 03067202 A2 | 8/2003 |
| WO | 2004055637 A2 | 7/2004 |
| WO | 2004061850 A1 | 7/2004 |
| WO | 2004084413 A2 | 9/2004 |
| WO | WO2005008505 | 1/2005 |
| WO | 2005031737 A1 | 4/2005 |
| WO | 2005048644 A2 | 5/2005 |
| WO | 2005031737 A1 | 7/2005 |
| WO | 2005109781 A1 | 11/2005 |
| WO | WO2006047697 | 5/2006 |
| WO | 2006071364 A1 | 6/2006 |
| WO | WO2006073891 | 7/2006 |
| WO | WO2006094380 | 9/2006 |
| WO | WO2007022421 | 2/2007 |
| WO | WO2007081514 | 7/2007 |
| WO | WO2007081515 | 7/2007 |
| WO | WO2007081524 | 7/2007 |
| WO | WO2007081526 | 7/2007 |
| WO | WO2007100707 | 9/2007 |
| WO | WO2007139660 | 12/2007 |
| WO | WO2007139738 | 12/2007 |
| WO | WO2008027834 | 3/2008 |
| WO | WO2008027910 | 3/2008 |

OTHER PUBLICATIONS

Office Action dated May 27, 2011 in U.S. Appl. No. 12/713,103.
Office Action dated Jan. 27, 2010 in U.S. Appl. No. 11/585,721.
Office Action dated Sep. 4, 2009 in U.S. Appl. No. 11/585,721.
Office Action dated May 13, 2009 in U.S. Appl. No. 11/585,721.
Notice of Allowance dated Dec. 31, 2009 in U.S. Appl. No. 11/683,391.
Office Action dated Sep. 17, 2009 in U.S. Appl. No. 11/683,391.
Office Action dated Apr. 2, 2009 in U.S. Appl. No. 11/683,391.
Office Action dated Oct. 29, 2008 in U.S. Appl. No. 11/566,072.
Application filed Jan. 9, 2007 U.S. Appl. No. 11/621,541.
Nonhoff/Arps, et al., "Straßenmusik Portable MP3/Spieler mit USB/Anschluss," CT Magazin Fuel Computer Technik, Verlag Heinz Heise GMBH, HannoveT DE, No. 25, Dec. 4, 2000.
Personal Jukebox (PJB), "Systems Research Center and PAAD," Compaq ComputeT Corp., Oct. 13, 2000, http://research.compaq.com/SRC/pjb/.
Peter Lewis, "Two New Ways to Buy Your Bits," CNN Money, Dec. 31, 2003, pp. 114.
Sastry, Ravindra Wadali. "A Need for Speed: A New Speedometer for Runners", submitted to the Department of Electrical Engineering and Computer Science at the Massachusetts Institute of Technology, May 28, 1999.
Sinitsyn, Alexander. "A Synchronization Framework for Personal Mobile Servers," Pervasice Computing and Communications Workshops, 2004. Proceedings of the Second IEEE Annual Conference on, Piscataway, NJ, USA, IEEE, Mar. 14, 2004, pp. 208/212.
SoundJam MP Plus, Representative Screens, published by Casady & Greene, Inc., Salinas, CA, 2000.
Specification Sheet, iTunes 2, Apple Computer, Inc., Oct. 31, 2001.
Spiller, Karen. "Low/decibel earbuds keep noise at a reasonable level", The Telegraph Online, dated Aug. 13, 2006, http://www.nashuatelegraph.com/apps/pbcs.dll/article?Date=20060813&-Cate . . . Downloaded Aug. 16, 2006.
Steinberg, "Sonicblue Rio Car," Product Review, Dec. 12, 2000, http://electronics.cnet.com/electronics/0/6342420/1304/4098389.html.
Travis Butler, "Archos Jukebox 6000 Challenges Nomad Jukebox," Aug. 13, 2001, http://db.tidbits.com/getbits.acgi?tbart=06521.
Travis Butler, "Portable MP3: The Nomad Jukebox," Jan. 8, 2001, http://db.tidbits.com/getbits.acgi?tbart=06261.
Orubeondo, "Trim AirCard 300 eases power demands," Infoworld, Nov. 29, 1999,3 pages.
"Sierra Wireless Announces First Cellular Network Interface Card for Notebook PCs; The AirCard 300 for Windows changes the Way Notebook PC Users Make Wireless Connections," Business Wire, Jun. 21, 1999, 2 pages.
Sierra Wireless advertisement for AirCard 300, in CIO magazine, Oct. 1, 1999, p. 90.
Sierra Wireless press release for AirCard 300, in Network World magazine, Aug. 23, 1999, p. 27.
Specification of the Bluetooth System, Specification vol. 1, v1.0 B, Dec. 1, 1999.
Specification of the Bluetooth System, Specification vol. 2, v1.0 B, Dec. 1999.
Palm-size PC User's Guide, Casio Computer Co 1999.
Clio C-l050 Series User Manual, Vadem, 1999.
EE Times, Issue 1047, pp. 4,20, and 22, Feb. 8, 1999, 126 pages.
Empeg Car User Guide, Empeg Limited, 1999, 19 pages.
Empeg Car, MP3 in your dash, Digital Audio Player User Guide, Empeg Limited, 2000, 50 pages.
Pegoraro, "Music Factory; Retailers Struggle to Expand Listening Options Online," Contra Costa Times, Mar. 19, 2000, Business Section, p. HOI.
eMusic.com Prospectus, 85 pages, Sep. 24, 1999.
Pegoraro, "Logging On; Setting Sound Free From the CD," The Washington Post, Mar. 3, 2000, Section Fast Forward, p. EOL.
Ericsson Inc., Research Disclosure, "Cellular phone with integrated MP3 player," Feb. 1999.

(56) References Cited

OTHER PUBLICATIONS

Digital cellular telecommunications system (Phase 2+); General Packet Radio Service (GPRS); Overall description of the GPRS radio interface; Stage 2 (GSM 03.64 version 6.0.1 Release 1997), 56 pages.
Digital cellular telecommunications system (Phase 2+); General Packet Radio Service (GPRS); Overall description of the GPRS radio interface; Stage 2 (GSM 03.64 version 6.1.0 Release 1997),42 pages.
Digital cellular telecommunications system (Phase 2+); General Packet Radio Service (GPRS); Overall description of the GPRS radio interface; Stage 2 (GSM 03.64 version 6.2.0 Release 1997),42 pages.
Digital cellular telecommunications system (Phase 2+); General Packet Radio Service (GPRS); Overall description of the GPRS radio interface; Stage 2 (GSM 03.64 version 6.3.0 Release 1997),42 pages.
Digital cellular telecommunications system (Phase 2+); General Packet Radio Service (GPRS); Overall description of the GPRS radio interface; Stage 2 (GSM 03.64 version 7.0.0 Release 1997),42 pages.
Cai et aL, "General Packet Radio Service in GSM," IEEE Communications Magazine, Oct. 1997, pp. 122-131.
IEEE Standard 802-11, Part 11; Wireless LAN Medium Access Control (MAC) and Physical Layer (PHY) specifications, 459 pages.
HP Jornada 420 palm-size PC User's Guide, Edition 1, 146 pages.
Lind, "the Network Vehicle—a Glimpse into the Future of Mobile Multi-Media," downloaded from IEEE Xplore on Dec. 17, 2009, pp. 121-1 thru 121-8.
Knudsen, "MP3 Linux Players," Linux Journal, online at http://www.linuxjournaLcom/article/3420, Jul. 1, 1999.
Menta, "1200 Song MP3 Portable is a Milestone Player," MP3 newswire.net, online at http://www.mp3newswire.net/stories/personaljuke.html, Jan. 11, 2000.
"MP3.com and i-drive. com join forces to store and manage MP3 files," Business Wire, Inc., Oct. 7, 1999.
MP3 Prospectus, Jul. 21, 1999.
Jeffrey, "Net Music Firms to Tap Public Market," Billboard Publications, Inc., Jul. 17, 1999.
"Digital Download Provider Muscimaker.com Partners With Download Directory Listen.com; Offers Nearly 100,000 Downloadable Tracks Via the Online Directory," PR Newswire Association, Inc., Sep. 15, 1999.
"Myplay, Inc. Launches Consumer Online Music Service; First in Industry to Focus on Ability to Centrally Store Music and Access it Via Multiple Devices; Company Secures Funding from Noted Venture Capital Firms," PR Newswire Association, Inc., Oct. 13, 1999.
"Myplay.com Launches Today; New Online Service Makes Downloading Digital Music Easy for Everyone; Sign up for Free Virtual Locker Get Bonus Tracks from Artists Including Kid Rock, Chirs Rock, Buckcherry Easy Access to your Music Collection for Download to Portable Media Players," PR Newswire Association, Inc., Oct. 13, 1999.
Nokia Press Release, "Nokia 5140 Mobile Phone adds mobility to Outdoor Adventure, Sport and Fitness," online at http://press.nokia.comlPR/200402/932564_5.html, Feb. 2, 2004.
Nokia 9110i User's Manual, Issue 3, 190 pages, copyright 1999.
Nokia Accessories Guide for the 9110 Communicator, Issue 3, 36 pages, copyright 1999.
Creative Nomad Digital Audio Player User Guide, Online Version, 40 pages, Version 1.0, Jun. 1999.
Creative Nomad II Getting Started Guide, 46 pages, Version 1.0, Jan. 2000.
PalmPilot Handbook, 3Com, Copyright 1997, 202 pages.
Qualcomm QCP-1960 User Guide, Apr. 1999, 79 pages.
RealNetworks, ReaUukebox Plus Manual, Copyright 1999, 88 pages.

RealPlayer 7 Plus User Manual, Revision 1.1, RealNetworks, inc., 2000,125 pages.
RealPlayer Plus G2 Manual, Revision 1.1, RealNetworks, Inc., 1998-1999,84 pages.
Rio 500 Getting Started Guide, for Windows 98 and Macintosh OS 8.6.
Rio PMP300 User's Guide, Diamond Multimedia Systems, Inc., 1998,28 pages.
Samsung SCH-3500 User's Guide, 111 pages.
Sony, VAIO Notebook Computer User Guide, PCG-731/PCG-735, 1998, 135 pages.
Sony, VAIO Notebook Computer User Guide, PCG-812, 1998, 144 pages.
Sony, VAIO Notebook Computer User Guide, PCG-838, 1999, 121 pages.
Sony Notebook Computer Service Manual, PCG-723/729, Sony Corporation, 1998.
Sony Notebook Computer Service Manual, PCG-731/735/737, Sony Corporation, 1998.
Sony Notebook Computer Service Manual, PCG-812/8I8, Sony Corporation, 1998.
Sony Notebook Computer Service Manual, PCG-838, Sony Corporation, 1999.
"Visteon: For Your Listening Pleasure—Any Music, Any Time, Anywhere," PRNewswire, Jan. 5, 2000.
NCKCN Windows 98 Second Edition Guide, http://www .nckcn.comlNCKCN/ie5/win98se/win982e.htm, downloaded Aug. 18, 2010.
Yamaha Music Sequencer QY70 Owner's Manual, 252 pages.
Yamaha QY Data Filer Owner's Manual, 30 pages.
Apple iTunes Smart Playlists, downloaded Apr. 5, 2005 from http://web.archive.org/web/20031002011316/www.apple.com/itunes/smartplaylists . . . pp. 1-2.
iTunes, Wikipedia: The Free Encyclopedia; downloaded on Oct. 5, 2005, pp. 1-6.
Nutzel et al., "Sharing Systems for Future HiFi Systems", The Computer Society, Jun. 2004.
Hart-Daves, Guy. "How To Do Everything With Your iPod and iPod Mini", 2004, McGraw-Hill Professional, p. 33.
"Apple Announces iTunes 2," Press Release, Apple Computer, Inc., Oct. 23, 2001.
"Apple Introduces iTunes 1 World's Best and Easiest To Use Jukebox Software," Macworld Expo, San Francisco, Jan. 9, 2001.
"Apple's iPod Available in Stores Tomorrow," Press Release, Apple Computer, Inc., Nov. 9, 2001.
"Nomad Jukebox," User Guide, Creative Technology Ltd., Version 1. Aug. 2000.
"SoundJam MP Plus Manual, version 2.0" 1 MP3 Player and Encoder for Macintosh by Jeffrey Robbin, Bill Kincaid and Dave Heller, manual by Tom Ne!lTino, published by Casady & Greene, Inc., 2000.
"12.1" 925 Candela Mobile PC", downloaded from LCDHardware.com on 12119/2002, http://www.lcdharware.com/panel/12_1_panel/default.asp.
"BL82 Series Backlit Keyboards", www.tg3electronics.com/products/backlit/backlit.htm, downloaded Dec. 19, 2002.
"Bluetooth PC Headsets—Enjoy Wireless VoIP Conversations: 'Connecting' Your Bluetooth Headset With Your Computer", Bluetooth PC Headsets; downloaded on 04129/06 from http://www.bluetoothpcheadsets.com/connect.htm.
"Creative MuVo TX 256 MB," T3 Magazine, Aug. 17, 2004, http://www.t3.co.uk/reviews/entertainment/mp3_player/creative_muvo_tx_256mb [downloaded Jun. 6, 2006].
"Digital Still Cameras—Downloading Images to a Computer," Mimi Chakarova et al., Multi/Media Reporting and Convergence, 2 pgs.
"Eluminx Illuminated Keyboard", downloaded Dec. 19, 2002, http://www.elumix.com/.
"How To Pair a Bluetooth Headset & Cell Phone", About.com; downloaded on Apr. 29, 2006 from http://mobileoffice.about.com/od/usingyourphone/ht/blueheadset_p.htm.

(56) References Cited

OTHER PUBLICATIONS

"Peripherals for Industrial Keyboards & Pointing Devices", Stealth Computer Corporation, downloaded on Dec. 19, 2002, http://www.stealthcomputer.com/peropherals_oem.htm.
"Poly/Optical Fiber Optic Membrane Switch Backlighting", downloaded Dec. 19, 2002, http://www.poly/optical.com/membrane_switches.html.
"Public Safety Technologies Tracer 2000 Computer", downloaded Dec. 19, 2002, http://www.pst911.com/traver.html.
Waterproof Music Player with FM Radio and Pedometer User Manual, Oregon Scientific, 2005.
"QuickTime Movie Playback Programming Guide", Apple Computer, Inc., Aug. 11, 2005.
"QuickTime Overview", Apple Computer, Inc., Aug. 11, 2005.
"Rocky Matrix Backlit Keyboard", downloaded Dec. 19, 2002, http//www.amrel.com/asi_matrixkeyboard.html.
"Sony Ericsson to introduce Auto pairing to improve Bluetooth connectivity between headsets and phones", Sep. 28, 2005 Press Release, Sony Ericsson Corporate; downloaded on Apr. 29, 2006 from http://www.sonyericsson.com/spg.jsp?cc=global&lc=en&ver=4001&template=pc3_1_1&z . . . .
"TAOS, Inc., Announces Industry's First Ambient Light Sensor to Convert Light Intensity to Digital Signals", www.taosinc.com/pressrelease_090902.htm, downloaded Jan. 23, 2003.
"Toughbook 28: Powerful, Rugged and Wireless", Panasonic: Toughbook Models, downloaded Dec. 19, 2002, http:www.panasonic.com/computer/notebook/html/01a_s8.htm.
"When it Comes to Selecting a Projection TV, Toshiba Makes Everything Perfectly Clear, Previews of New Releases", www.bestbuv.comlHomeAudio Video/Specials/ToshihIITVFeatures.asJ2, downloaded Jan. 23, 2003.
"WhyBuy: Think Pad", IBM ThinkPad Web Page Ease of Use, downloaded on Dec. 19, 2002, http://www.pc.ibm.com/us/thinkpad/easeofuse.html.
512MB Waterproof MP3 Player with FM Radio & Built/in Pedometer, Oregon Scientific, downloaded on 07/31106 from www2.oregonscientific.com/shop/product.asp?cid=4&scid=11&pid=581.
Adam C. Engst, "SoundJam Keeps on Jammin'," Jun. 19, 2000, http://db.tidbits.com/getbits.acgl?tbart=05988.
Alex Veiga, "AT&T Wireless Launching Music Service," Yahoo! Finance, Oct. 5, 2004, pp. 112.
Andrew Birrell, "Personal Jukebox (PJB)," Oct. 13, 2000, http://birrell.org/andrew/talks/pjb/overview.ppt.
Apple iPod Technical Specifications. iPod 20GB and 60GB Mac + PC, downloaded from http://www.app1e.comlipod/coJor/specs.html on Aug. 8, 2005.
Bociurkiw, Michael, "Product Guide: Vanessa I\tlatz,", www.forbes.com/asao!2000i1127ivmartz mint.html, Nov. 27, 2000.
Compaq, "Personal Jukebox," Jan. 24, 2001, httlrllresearch.comQag.com/SRC/gjb/.
Creative: "Creative NOMAD MuVo TX," www.creative.com, Nov. 1, 2004, http://web.archive.org/web/20041024175952/www.creative.comlproducts/pfriendly.asp?product=9672 [downloaded Jun. 6, 2006].
Creative: "Creative NOMAD MuVo," www.creative.com, Nov. 1, 2004, http://web.archive.org/web/20041024075901/www.creative.comlproducts/product.asp?category=213&subcategory=215&product=110 [downloaded Jun. 7, 2006].
Creative: "MP3 Player," www.creative.com, Nov. 1, 2004, http://web.archive.org/web/20041024074823/www.creative.comlproducts/product.asp?category=213&subcategory=216&product=4983 [downloaded Jun. 7, 2006].
De Herrera, Chris, "Microsoft ActiveSync 3.1." Version 1.02, Oct. 13, 2000.
iAP Sports Lingo O×09 Protocol V1.00, May 1, 2006.
IEEE 1394—Wikipedia, 1995, http://www.wikipedia.org/wiki/Firewire.
iTunes 2, Playlist Related Help Screens, iTunes v2.0, Apple Computer, Inc., Oct. 23, 2001.
Jabra Bluetooth Headset User Manual; GN Netcom AIs, 2005.
Jabra Bluetooth Introduction; GN Netcom AIS, Oct. 2004.
Jabra FreeSpeak BT200 User Manual; Jabra Corporation, 2002.
Kennedy, "Digital Data Storage Using Video Disc," IBM Technical Disclosure Bulletin, vol. 24, No. 2, Jul. 1981.
Miniman, "Applian Software's Replay Radio and Player v1.02," Product review, pocketnow.com, http://www.pocketnow.com/reviewsireplay/replay.htm, Jul. 31, 2001.
Musicmatch, "Musicmatch and Xing Technology Introduce Musicmatch Jukebox," May 18, 1998, http://www.musicmatch.comJinfo/collDanyipressireleasesF'year=1998&reJease=2.
Anonymous: "Itunes keeps track of your tastes" Internet citation Online Oct. 2 (Oct. 2, 2003), XP002328080 Retrieved from the Internet: URL: http://web.archive.org/web/20031002011316/http://www.apple.com/itunes/smartplaylists.html> [retrieved on May 4, 2005] the whole document.
Paradiso et al., Design and Implementation of Expressive Footwear, May 12, 2000, IBM Systems Journal, vol. 39, Nos. 3 & 4, pp. 1-49.
NKCN Windows 98 Second Edition Guide http://www.nckcn.com/NCKCN/i.e.5/win98se/win982e.htm, downloaded Aug. 18, 2010.
Shannon P. Jackson and Harold Kirkham, "Weighing Scales Based on Low-Power Strain-Gauge Circuits", NASA Tech Briefs, Jun. 2001, p. 49 US.
No author listed, "Your Next . . . ", Newsweek, Jun. 25, 2001, p. 52-54 plus cover US.
Wikipedia: "Itunes" Internet Citation [Online] May 10, 2005 (May 10, 2005), XP002327815 Retrieved from the Internet: URL: http://en.wikipedia.org/wiki/Itunes> [retrieved on May 11, 2005} the whole document.
Sony Notebook Computer Service Manual, PCG-717/719, Sony Corporation, 1997.
Digital StarTAC Wireless Telephone User Manual, Motorola, Mar. 1999, 19 pages.
SELLERS. Gear to Go, Mitch Mandel Photography, Mar. 2001, pp. 61-62.
Sharp, A Sense of the Real World, www.idsystems.com/reader/2000_09/sens0900.htm, Sep. 2000, 4 pages.
Skaloud et al., DGPS-Calibrated Accelerometric System for Dynamic Sports Events, Sep. 19-22, 2000, ION GPS 2000.
Smith et al., "Flexible and Survivable Non-Volatile Memory Data Recorder", AFRL Technology Horizons, Dec. 2000, p. 26.
Webster's II New Riverside University Dictionary, 1988, The Riverside Publishing Company, p. 1138.
Wysocki, Jr., Staff Reporter, "Do Devices Measuring Body Signs Appeal to the Sick or Healthy", Pittsburgh, US.
No author listed, "Ever Forget to Bring Your Cell Phone or Keys?", Catalog Page, PI Manufacturing Corp, 20732 Currier Rd., Walnut, CA 91789, Home Office Accessory, Catalog Nos. TA-100N; TA-100M; TA-100F, US.
No author listed, WarmMark Time Temperature Indicators, www.coldice.com/warmmark_temperature indicators.html, Cold Ice, Inc.
No author listed, Wireless Temperature Monitor, www.echo-on.net/mob/, Nov. 20. 2000.
Unattributed, 3M MonitorMark Indicator Data Sheet [online], [retrieved on Aug. 9, 2004], retrieved from the Internet: URL: http://www.3m.com/us/healthcare/medicalspecialties/monitor/products.html; 4 pages.
Desmarais, "Solutions in Hand", BEI Technologies, Inc., www.sensormag.com, Jan. 2001, pp. 1-2.
Desmarais et al., "How to select and use the right temperature," www.sensorsmag.com, Jan. 2001, pp. 30-36.
GPS Locator for Children, Klass Kids Foundation Jul. 15, 2004.
Henkel, Research & Developments, Sensors, Nov. 2000. p. 18.
Licking, Special Report: E-Health, "This is the Future of Medicine", Business Week E.Biz, Dec. 11, 2000, pp. 77 and 78 US.
Li-Ron, Tomorrow's Cures, Health & Fitness Special Section Online, Newsweek, Dec. 10, 2001, pp. 3-10.
Mark of Fitness Flyer, "High Quality, Self-Taking Blood Pressure Monitors", four pages, Shrewsbury, NJ, US.
Martella, Product News, "Temperature Monitoring System", Nov. 2000, p. 77.
SoundJam MP Digital Audio System User Guide, Mac Utility, 1999, 52 pages.

(56) References Cited

OTHER PUBLICATIONS

Paradiso, et al. "Instrumented Footwear for Interactive Dance" Version 1.1, Presented at the XII Colloquium on Musical Informatics, Gorizia, Italy, Sep. 24-26, 1998, pp. 1-4.
Paradiso et al., Design and Implementation of Expressive Footwear, May 12, 2000, IBM Systems Journal, vol. 39, Nos. 3 & 4, pp. 511-529.
Nobbe, "Olympic Athletes Get a Boost from Technology", Machine Design, vol. 60, No. 19, Aug. 25, 1988.
No author listed, The GPS Connection, Popular Mechanics, Feb. 2001, p. 65.
No author listed, "Your Next . . . ", Newsweek, Jun. 25, 2001, p. 52 US.
Janssens et al., "Columbus: A Novel Sensor System for Domestic Washing Machines", Sensors Magazine Online, Jun. 2002, pp. 1-9.
iTunes, Playlist Related Help Screens, iTunes v1.0, Apple Computer, Inc., Jan. 2001.
Deem, "Fast Forward Go for a Ride on The World's Fastest Sailboat", Popular Mechanics, www.popularmechanics.com, Feb. 2001, pp. 1-2.
Cole, George, "The Little Label with an Explosion of Applications", Financial Times, Ltd., 2002, pp. 1-3.
Civil Action No. 07-CV-00238; Nike Inc.'s Answer, Affirmative Defenses to First Complaint, Mar. 19, 2007.
Civil Action No. 07-CV-00238-REB-PAC, Complaint, Mar. 19, 2007.
Civil Action No. 07-CV-00238-REB, Apple Inc.'s Answer to Complaint, Counterclaims and Jury Demand, Mar. 19, 2007.
Civil Action No. 07-CV-00078-MSK-BNB, Complaint, Jan. 12, 2007.
Civil Action No. 07-CV-00078-MSK-BNB, Answer, Feb. 9, 2007.
Civil Action No. 06-CV-02122-REB-MJW, Complaint, Oct. 24, 2006.
Civil Action No. 06-CV-02122-REB-MJW, Apple Computer, Inc.'s Answer to Complaint and Counterclaims, Jan. 22, 2007.
Civil Action No. 06-CV-01447-MSK-BNB; Timex Disclosure Statement; Sep. 26, 2006.
Civil Action No. 06-CV-01447-MSK-BNB; Gamin Disclosure Statement; Sep. 26, 2006.
Civil Action No. 06-CV-01447-MSK-BNB: PhatRat Technology, Inc.'s Supplemental Answers and Objections to Defendant, Timex Corporation's Interrogatories Nos. 1, 2, 5, 7-11, 13 and 15; Feb. 12, 2007.
Civil Action No. 06-CV-01447-MSK-BNB, Complaint, Jul. 26, 2006.
Civil Action No. 06-CV-01447-MSK-BNB, Answer, Affirmative Defenses, Counterclaim, and Demand for Jury Trial, Garmin; Sep. 26, 2006.
Civil Action No. 06-CV-01447 MSK-BNB, First Amended Complaint; Aug. 16, 2006.
Civil Action No. 06-CV-01447 MSK-BNB, Answer, Affirmative Defenses, Counterclaims and Demand for Jury Trial, Timex; Sep. 26, 2006.
Civil Action No. 06-CV-01100-WDM-PAC, Defendants Polar Electro Inc.'s and Polar Electro Oy's Answer and Affirmative Defenses: Polar Electro Inc.'s Counterclaim and Demand for Jury Trial, Jun. 29, 2006.
Civil Action No. 06-CV-01100-WDM-PAC, Complaint, Jun. 8, 2000.
Civil Action No. 05-CV-02323; Complaint, Nov. 16, 2005.
Bociurkiw, Michael, "Product Guide: Vanessa Matz,", www.forbes.com/asap/2000/1127/vmartzprint.html, Nov. 27, 2000.

* cited by examiner

| Workout id 604 | Workout characteristics | |
|---|---|---|
| | Template 608 | Playlist 610 |
| | | |
| | | |

| Playlist 654 | Playlist 656 | Behavior 658 |
|---|---|---|
| | | |
| | | |

# INTEGRATED MEDIA JUKEBOX AND PHYSIOLOGIC DATA HANDLING APPLICATION

RELATED APPLICATIONS

This application is a continuation application of, and hereby claims priority to, pending U.S. patent application Ser. No. 13/605,939, titled "Integrated Media Jukebox and Physiologic Data Handling Application," by the same inventors, which was filed on 6 Sep. 2012. The application is also a divisional application of and claims priority to now-abandoned U.S. patent application Ser. No. 11/419,737, titled "Integrated Media Jukebox and Physiologic Data Handling Application," by the same inventors, which was filed on 22 May 2006, to which parent application Ser. No. 13/605,939 also claims priority. Both of these applications are incorporated by reference.

This application is related to U.S. patent application Ser. No. 11/566,072, filed 22 May 2006, and entitled "Activity Monitoring System", which is hereby incorporated by reference herein. This application is also related to U.S. patent application Ser. No. 11/439,521, filed 22 May 2006, and entitled "Communication Protocol for Use with Portable Electronic Devices", which is hereby incorporated by reference herein.

BACKGROUND OF THE INVENTION

The use of devices to obtain exercise performance information is known. For example, simple mechanical pedometers have been used to obtain information relating to walking or running. A typical mechanical pedometer is a standalone device merely displays an indication of number of steps taken which, typically at most, can be converted to distance traveled by multiplying the number of steps taken by an estimated average stride size.

Recently, more sophisticated devices are known. For example, as described in U.S. Pat. No. 6,898,550 (the '550 patent), a foot-mounted unit, including a sensor for sensing motion of the foot of a user, is configured to provide motion information wirelessly—to a wrist-mounted unit. The wrist-mounted unit includes a display for displaying information to the user based upon data accumulated by the foot-mounted unit and transmitted wirelessly to the wrist-mounted unit. In addition, as described in the '550 patent, the wrist-mounted unit may be coupled to a computer and/or a network server via a network. The user can operate software running on the computer and/or the server to analyze received data and/or to select operating parameters for the wrist-mounted unit and/or the foot-mounted unit.

The inventors have realized that a media jukebox computer application, including functionality to interact with a portable media player, may be synergistically combined with functionality to handle physiologic data from a physiologic data gathering device that is in communication with the portable media player for providing physiologic data to the portable media player.

SUMMARY

A method is provided to operate a computer to interoperate with a portable media player. The method includes processing signals provided from the portable media player to the computer that are indicative of whether an accessory has been connected to the portable media player, to determine whether the accessory has been connected to the portable media player. Based on a determination that the accessory has been connected to the portable media player, physiologic data of a user that was provided to the portable media player from a wireless physiologic data gathering device, is received from the portable media player, into the computer, via the accessory.

BRIEF DESCRIPTION OF THE DRAWINGS

FIGS. 6a and 6b illustrate, in accordance with some examples, data structures that may be maintained within a portable media player, usable to correlate measurement and/or control of physical activity with playback of media.

DETAILED DESCRIPTION

Figure 1:
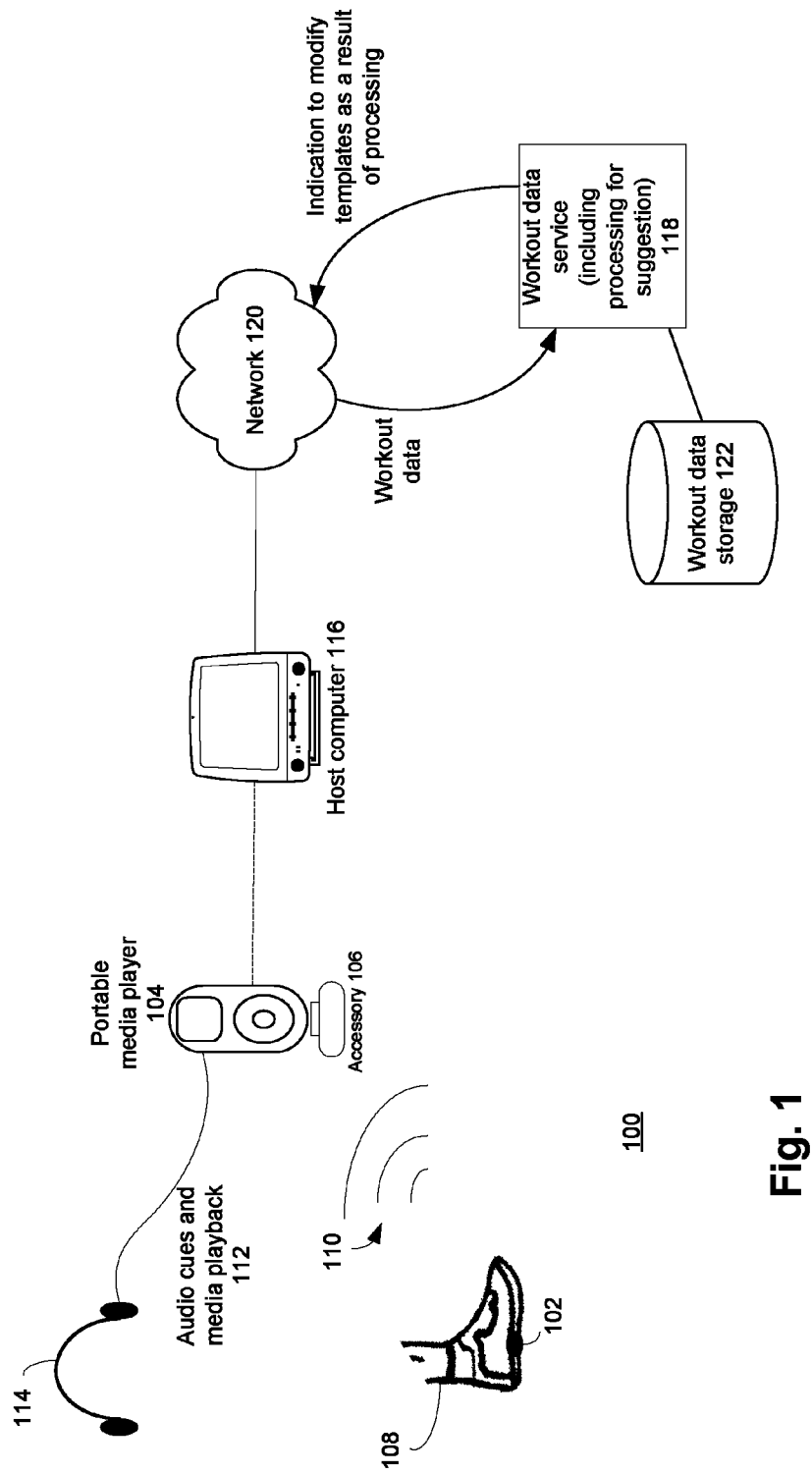
FIG. 1 illustrates an example of a system, including a portable media player, generally usable for, among other things, monitoring and/or controlling user exercise or other activity or physiology.

FIG. 1 illustrates an example of a system 100, including a portable media player 104, generally usable for, among other things, monitoring and/or controlling user exercise or other activity or physiology. Referring to FIG. 1, user exercise data is communicated (in this example, wirelessly) from a data gathering device 102, configured for gathering physiological data of a user (such as a sensor to sense the foot motion of a user), to the portable media player 104. In one example, the wireless communication is via an accessory 106, configured to selectively attach to a data port of the portable media player 104. An example of the accessory 106, and the interoperation of the accessory with the portable media player 104, is described in some detail in related U.S. patent application Ser. No. 11/439,521, filed 22 May 2006, and entitled "COMMUNICATION PROTOCOL FOR USE WITH PORTABLE ELECTRONIC DEVICES", referenced above, and incorporated by reference herein, in the section entitled "Cross Reference to Related Applications."

In operation, while a user 108 is exercising, physiological data of the user is accumulated by the data gathering device 102 and is provided wirelessly (via radio frequency waves 110, in one example) to the portable media player 104. Meanwhile, cues relative to the exercise (e.g., audio cues) as indicated by exercise templates, are being provided from the portable media player 104 to the user 108 (e.g., via a wire 112 and headphones 114). In addition to providing the cues relative to the exercise, the portable media player 104 may also be configured to provide playback of media (such as audio media) to the user 108 (e.g., like with the audio cues, via the wire 112 and headphones 114).

The playback of media may be coordinated with the exercise cues. For example, the playback of media may be using a playlist such as created using the iTunes® software application, provided by Apple Computer, Inc., running on a host computer 116 connectable to the portable media player 104. The playlists may be incorporated with, or corresponded to, the exercise templates on which the exercise cues are based.

Going in the direction from the portable media player 104 to the host computer 116, the portable media player 104 is configured to provide physiologic data to a workout data service 118, for storage 122, via the host computer 116 and a network 120 such as the internet. In some examples, the host computer 116 operates substantially as a conduit for providing the physiologic data to the workout data service 118 for storage 122. In other examples, the host computer 116 performs some processing on the physiologic data, temporarily stores the physiologic data for later forwarding (e.g., during a temporary loss of connection between the host computer 116 and the service 118 via the network 120), or both.

In yet other examples, not explicitly represented in FIG. 1, the physiological data is never or is only selectively provided to a service such as the workout data service 118. That is, the physiologic data may be maintained in storage on the portable media player 104, on the host computer 116, on both or on neither.

In still other examples, the physiological data is provided from the portable media player 104 to the workout data service 118 without being provided to a host computer such as the host computer 116. For example, the portable media player 104 may be incorporated into or, may be incorporated with, a telephone or other communication device that is connectable (e.g., wirelessly) to the workout data service 118.

With regard to the workout data service 118 and storage 122, in some examples, the physiologic data is processed at the workout data service 118. In one example, the physiologic data from one user is processed in view of physiologic data from other users to, for example, compare the users in terms of the physiologic data. In another example, the physiologic data is processed at the workout data service 118 to determine a suggested template change. For example, based on the processing at the workout data service 118, it may be suggested to change the clues to provide motivation at a particular portion of the workout. As another example, based on playlists associated with that workout by other users, a different playlist (or changes to the playlist) may be suggested for a particular workout.

Figure 2:
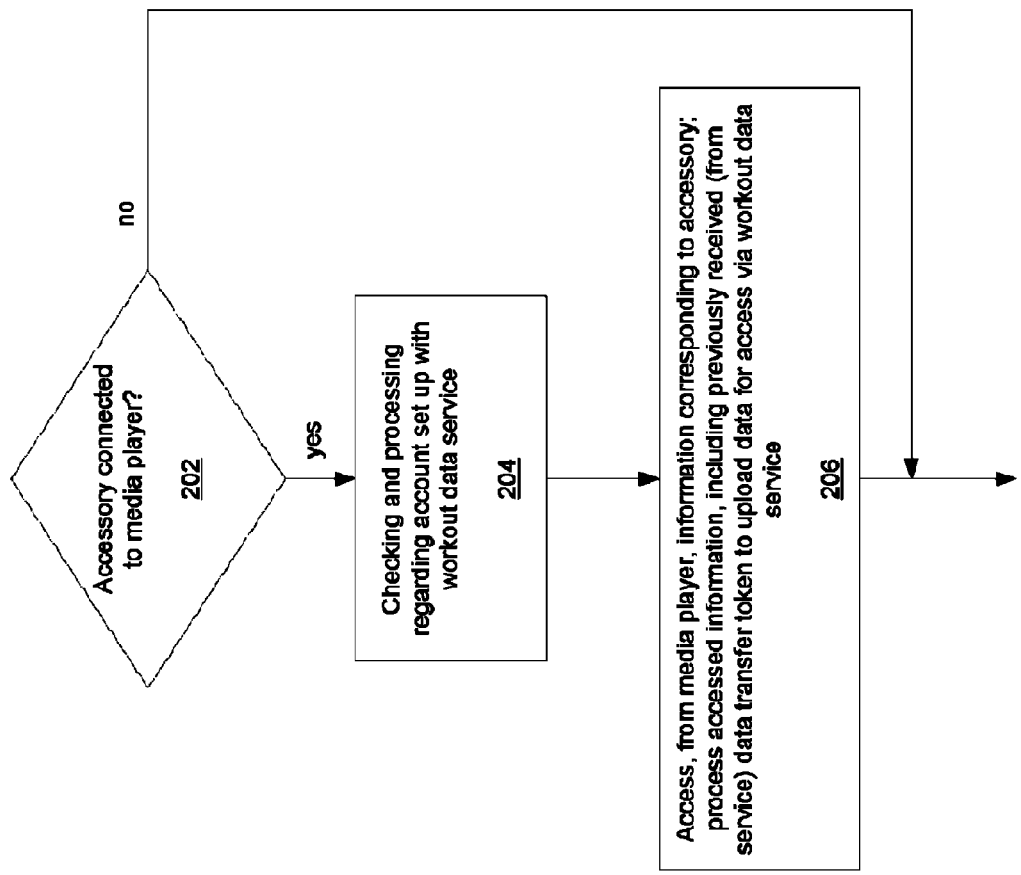
FIG. 2. is a flowchart illustrating an example of steps, mostly within a host computer, to accomplish transfer of physiologic data between a portable media player and a workout data service.

FIG. 2. is a flowchart 200 illustrating an example of steps, mostly within the host computer 116, to accomplish transfer of physiologic data between the portable media player 104 and the workout data service 118. At step 202, it is determined whether the accessory 106 has been connected to the portable media player 104, which would allow the physiological data to be received by the portable media player from the data gathering device 102.

The determination of whether the accessory 106 has been connected is, in one example, via configuration data that is provided to the host computer 116 when the portable media player 104 and the host computer 116 are connected, in a portion of a handshake protocol in which the portable media player 104 provides information to the host computer 116 regarding characteristics, capabilities and/or activities of the portable media player 104. In other examples, the accessory 106 is one of a plurality of possible accessories, and the check for the accessory 106 is merely part of a check for accessories generally. In yet other examples, mentioned below, processing like that in step 202 is not carried out at all.

If it is determined at step 202 that the accessory 106 has not been connected to the portable media player 104, then the FIG. 2 processing ends. Otherwise, if it is determined at step 202 that the accessory 106 has been connected to the portable media player 104, or if step 202 is not performed at all, then processing continues at step 204, to match the portable media player 104 to an account of the workout data service 118. At step 204, a check is made for an account for the user at the workout data service 118. If it is determined at step 204 that the user does not have an account at the workout data service 118, then the step 204 processing includes causing interaction with the user to set up an account at the workout data service 118. At step 206, the host computer accesses the physiologic data, if any, stored in the portable media player 104 (e.g., from a preset location of storage within the portable media player 104) and provides the physiologic data to the workout data service 118 to be associated with the user's account. In some examples, if a connection to the workout data service 118 is not available (e.g., there is no connection between the host computer 116 and the network), then step 206 is prevented from being performed.

The physiologic data may be provided from the portable media player 104 to the host computer 116, and further to the workout data service 118, in an XML-formatted file. In some examples, a portion of the provided data is retained on the portable media player 104, for easy reference by the user (e.g., during or in preparation for a workout). Communication between the host computer 116 and the workout data service 118 is typically via Secure Socket Layer, using the HTTPS protocol. In one example, a portion of the physiologic data is retained in storage of the portable media player 104 (e.g., the last "n" workouts) and can be displayed via a user interface of the portable media player 104. Furthermore, while the physiologic data is passed on to the workout data service 118 from the host computer 116, the host computer 116 may retain some or all of the physiologic data to, for example, display the data via a physiologic data user interface of a music store application operating on the host computer 116. An example user interface display of the music store application operation on the host computer 116, including a display of physiologic data, is described later, with reference to FIG. 8.

Figure 3:
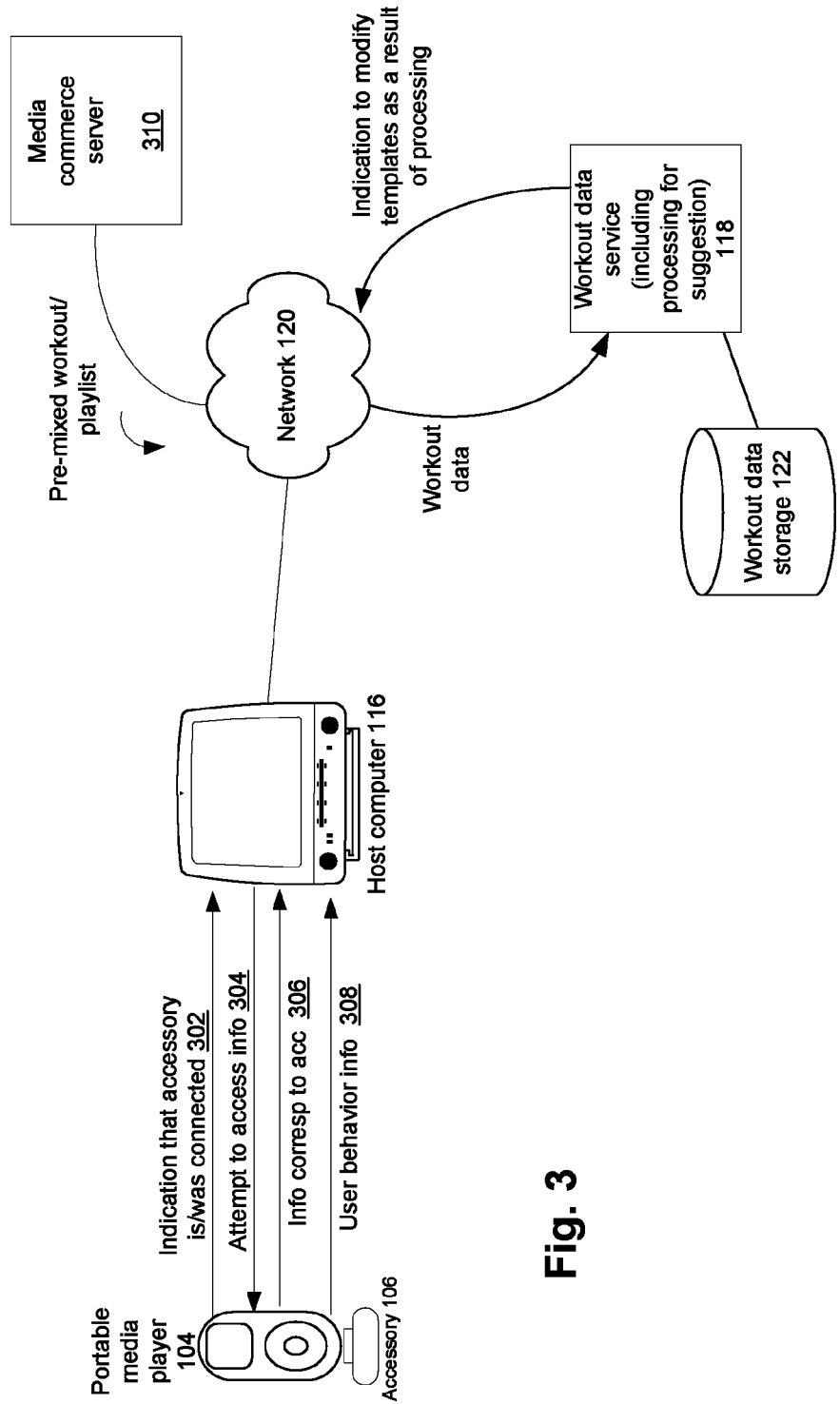
FIG. 3 is a schematic diagram that, while similar to FIG. 1, illustrates details of example configuration and operation of particular portions of the FIG. 1 system.

FIG. 3 is a schematic diagram that, while similar to FIG. 1, illustrates details of example configuration and operation of particular portions of the FIG. 1 system. As shown in FIG. 3, there are a number of signals involved in interoperation of the portable media player 104 and the host computer 116. A signal 302 is provided from the portable media player 104 indicating that the accessory 106, via which the data gathering device 102 (FIG. 1) communicates with the portable media player 104 is or was attached to the portable media player 104. The signal 304 represents an attempt by the host computer 116, in response, to access information on the portable media player 104 corresponding to the accessory 106 (i.e., physiologic data provided to the portable media player 104 from the data gathering device 102 via the accessory 106). The signal 306 represents the information corresponding to the accessory being provided from the portable media player 104 to the host computer 116.

In addition, the signal 308 represents feedback of user behavior information relative to the playback of media (which may also correspond to use/operation of the device 102 that provides physiologic data via the accessory 106) and, concomitantly, relative to the exercise cues. This feedback user behavior information signal 308 may be 8 used to modify (or suggest modifications to) the play lists, templates, or some combination thereof, based on the user's behavior as indicated by the signal 308. The modifications and/or suggested modifications may be a result of processing within the host computer 116 or, as discussed above, the modifications and/or suggested modifications may be a result of processing within the workout data service 118 (typically resulting from processing of physiologic data from the particular user and related data from a community of users, and not just from processing of physiologic data and related data from the particular user alone).

It is noted that, as alluded to above, while FIGS. 2 and 3 illustrate detecting whether the accessory 106 is or was connected to the portable media player 104, there are other examples in which the host computer 116 and the portable media player 104 interoperate such that the host computer 116 can determine whether there may be physiologic data, from the data gathering device 102, present on the portable media player to be provided to the host computer 116. For example, the host computer 116 may initiate a check in a predetermined area of the portable media player 104 storage (e.g., in a particular directory) for physiologic data for retrieval.

As also shown in FIG. 3, the host computer 116 may communicate with a media commerce service 310, via the network 120, to accomplish the purchase of exercise templates, which may also be combined with or otherwise indicate associated playlists. In this way, prepackaged workout/song mixes may be purchased. While the templates and playlists are typically purchased, there are circumstances in which the templates and playlists may be provided without cost (e.g., promotions).

Figure 4:
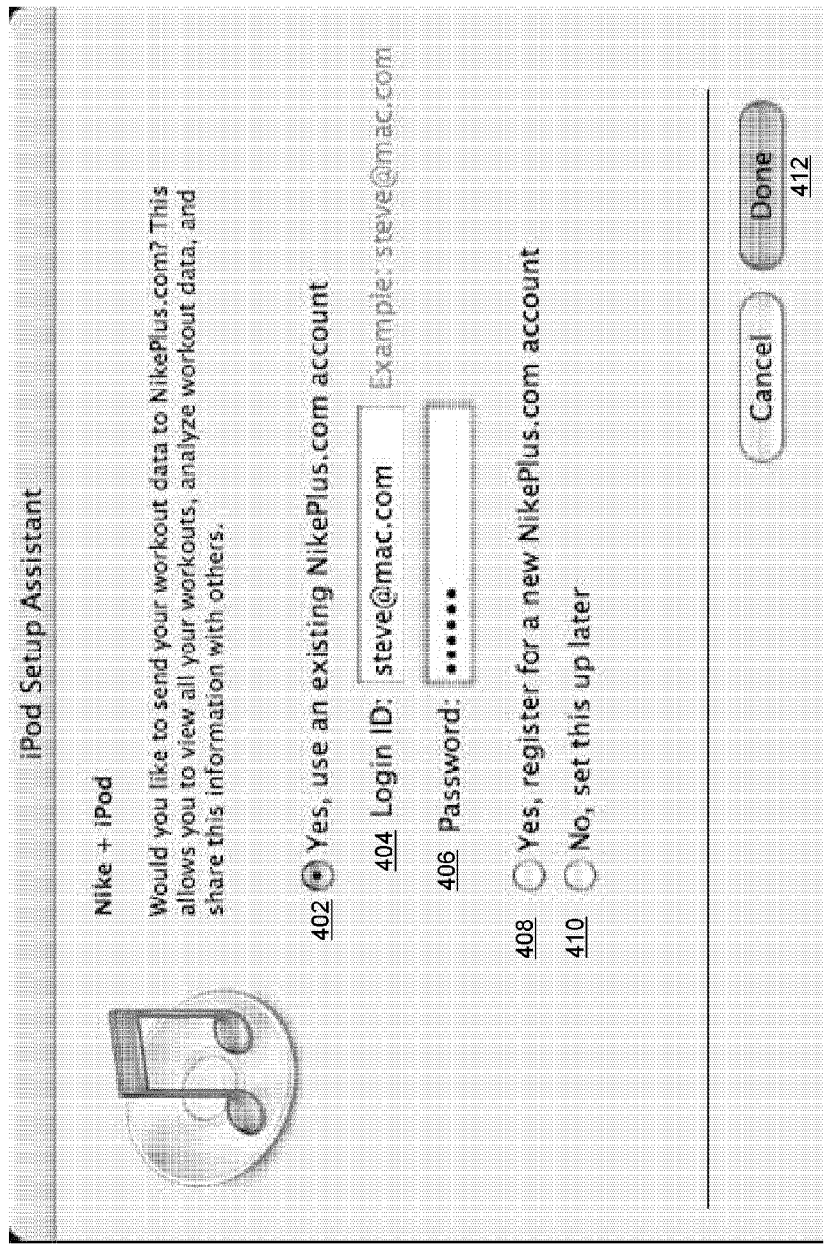
FIG. 4 is a screenshot that illustrates an example of a user interface of an application (such as a media jukebox application) on a host computer that may be provided to accomplish an account matching between a portable media player and a workout data service.

FIG. 4 is a screenshot that illustrates an example of a user interface of an application on the host computer 116 that may be provided to accomplish the account matching (step 204, in FIG. 2) between the portable media player 104 and the workout data service 118. The application may be, for example, a media jukebox application such as the iTunes® application, as discussed above. Referring to FIG. 4, an application in the host computer 116 displays a setup screen 400 to accomplish associating the physiologic data corresponding to a particular user with an account for that user at the workout data 9 service 118. As can be seen from the FIG. 4 screenshot 400, if the user has a preexisting account with the workout data service 118, the user selects the radio button 402, and provides a login ID 404 and password 406 associated with the preexisting account. To register for a new account, the user selects the radio button 408, which (after selecting the "Done" button 412), causes presentation of an account creation page of the workout data service 118. The user indicates the account credentials (such as username and password) so that the physiologic data may be passed from the host computer 116 to an account at the workout data service 118 associated with the user. As also illustrated in FIG. 4, an option (radio button 410) is also provided to postpone the account access setup.

Once an account is matched between the portable media player 104 and the workout data service 118 for physiologic data received by the portable media player 104 via the accessory 106, account access credentials may be saved at the host computer 116 for later use. The account access credentials may even be saved at the portable media player 104 (to, for example, be subsequently provided to the host computer 116 along with physiologic data). In one example, account access credentials such as login ID and password are not themselves saved on either the host computer 116 or the portable media player 104. Rather, the workout data service 118 provides back to the host computer 116 an account access "token" that uniquely corresponds to the account access credentials and that provides only limited access to the workout data service 118, for providing physiologic data to the workout data service 118. For example, the full account access credentials may provide access to workout data service 118 functions such as ecommerce or other security-sensitive functions, for which it may be considered undesirable to store access credentials on the host computer 116 or on the portable media player 104.

Figure 5:
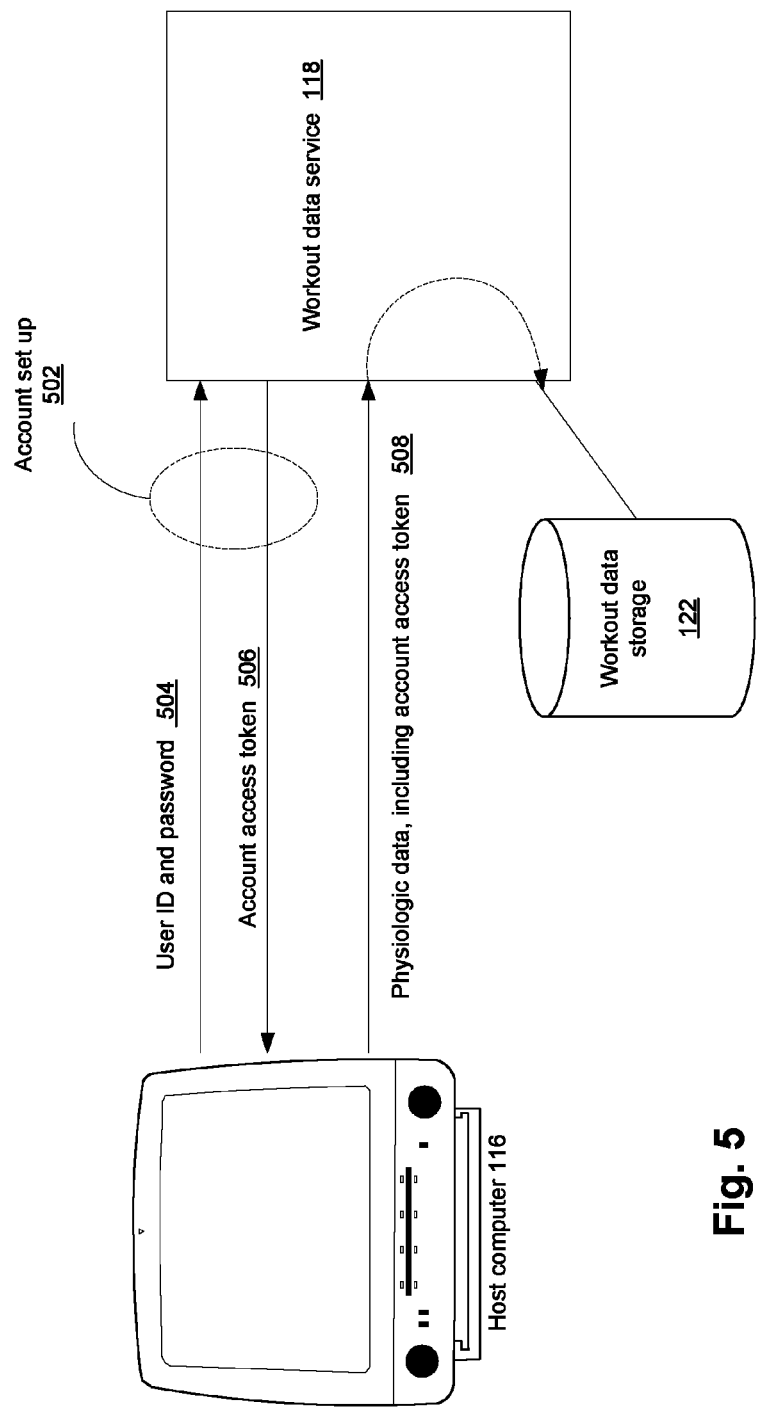
FIG. 5 schematically illustrates an example of signals involved in an interaction between a host computer and a workout data service with regard to account setup (FIG. 4) and use of an account access token.

FIG. 5 schematically illustrates an example of signals involved in the interaction between the host computer 116 and the workout data service 118 with regard to account setup (FIG. 4) and use of an account access token. The dashed oval 502 represents a portion of the account set up interaction between the host computer 116 and the workout data service 118. Specifically, arrow 504 represents account credentials (such as user ID and password) being provided from the host computer 116 to the workout data service 10 118. An account access token, corresponding to the account credentials) is provided back to the host computer 116 from the workout data service 118. In operation, to provide physiologic data to the workout data service 118 for storage 122, the account access token is provided to the workout data service 118 in conjunction with the physiologic data 508. As mentioned above, the workout data service 118 uses the account access token to grant limited access to the workout data service 118, for example, for storing the physiologic data and for associated analysis and/or viewing functions.

FIGS. 6a and 6b illustrate, in accordance with some examples, data structures that may be maintained within the portable media player 104, usable to correlate measurement and/or control of physical activity with playback of media. For example, the data structures may include a table 602 and a table 652. Each row of the table 602 is indexed by a workout id, in column 604. A workout id refers to a particular distinguishable workout, as now discussed. For example, for a particular workout (identified by a workout id), the column 606 (in one example, including two columns 608 and 610, as discussed shortly) includes an indication of workout characteristics.

In the FIG. 6a example, the workout characteristics in column 606 include a template designation 608 and a playlist designation 610. As discussed above, a template indicates cues, such as audio cues, corresponding to a particular workout. The playlist designation 610 indicates a play list, defining media playback associated with the workout.

FIG. 6b includes a table 652 of playlists maintained in the portable media player 104. The column 654 includes the playlist designation for each playlist. The column 656 indicates the media (typically, songs) corresponding to each playlist. The column 658 includes an indication of the user's behavior relative to the playlist. For example, the column 658 may indicate a workout id, that indicates a workout during which the user played the songs of the playlist (or, songs generally, even if not part of a playlist). As another example, the column 658 may includes an indication of user behavior to override the playlist, such as behavior to cause songs to be skipped. Referring back to FIG. 3, this user behavior information may be provided to the host computer 116 such that processing within the host computer 116 modifies play lists, forms play lists, associates playlists with workouts, or other results as appropriate, based on the user behavior information.

Figure 7:
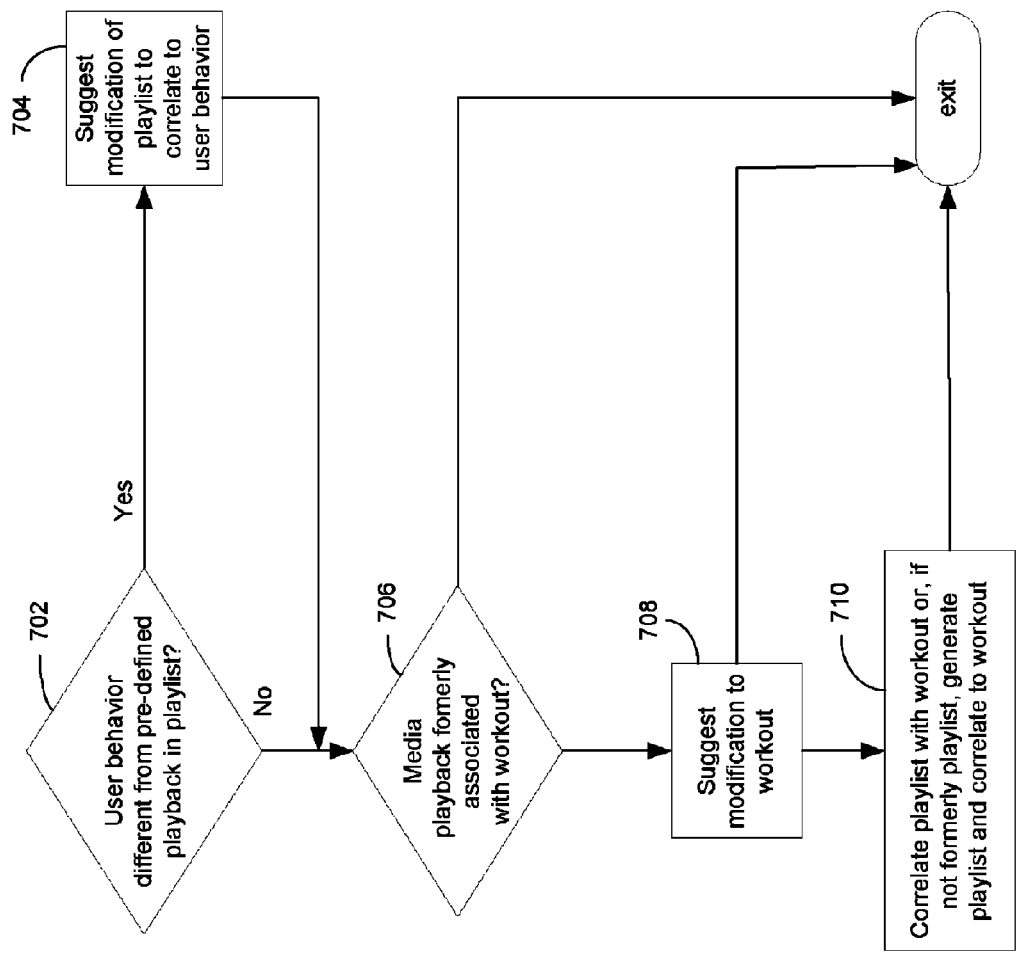
FIG. 7 is a flowchart illustrating an example of processing within a host computer to process user behavior information and other data in the FIG. 6 data structures.

FIG. 7 is a flowchart illustrating an example of processing within the host computer 116 to process the user behavior information and other data in the FIG. 6 data structures. At step 702, it is determined if the actual user behavior is different from the pre-defined playback behavior indicated by the corresponding playlist. For example, if the user behavior information indicates that the user overrode the playlist by skipping songs, then processing within the host computer 116, at step 704, suggests to the user, via a user interface, to allow playlist to be modified to correlate to the user behavior.

In some examples, the user behavior information may not be clearly indicative of a definite suggestion at step 704. For example, the user may have skipped one song each of ten times of processing the play list, whereas the user may have skipped a second song only one time of processing the play list. The suggestions may provide gradations of suggestion. For example, it may be strongly suggested to delete the first song (the one skipped ten times) from the playlist, whereas it may be mildly suggested to delete the second song (the one skipped only one time) from the playlist.

In the next steps shown in the FIG. 7 flowchart, processing is carried out to suggest associating a play list with a particular workout, based on the media playback as controlled manually by the user, during the particular workout. At step 706, it is determined from the user behavior information if the media playback during a workout (i.e., during processing of a particular workout template by the portable media player 104) corresponds to a pre-existing playlist. If so, then processing of FIG. 7 exits. If it is determined at step 706 that the media playback during the workout does not correspond to a pre-existing playlist then, at step 708, a correlation to the workout (i.e., to the template) is suggested. If the user agrees then, at step 710, the media playback is associated with a play list, and that playlist is associated with the workout.

Figure 8:
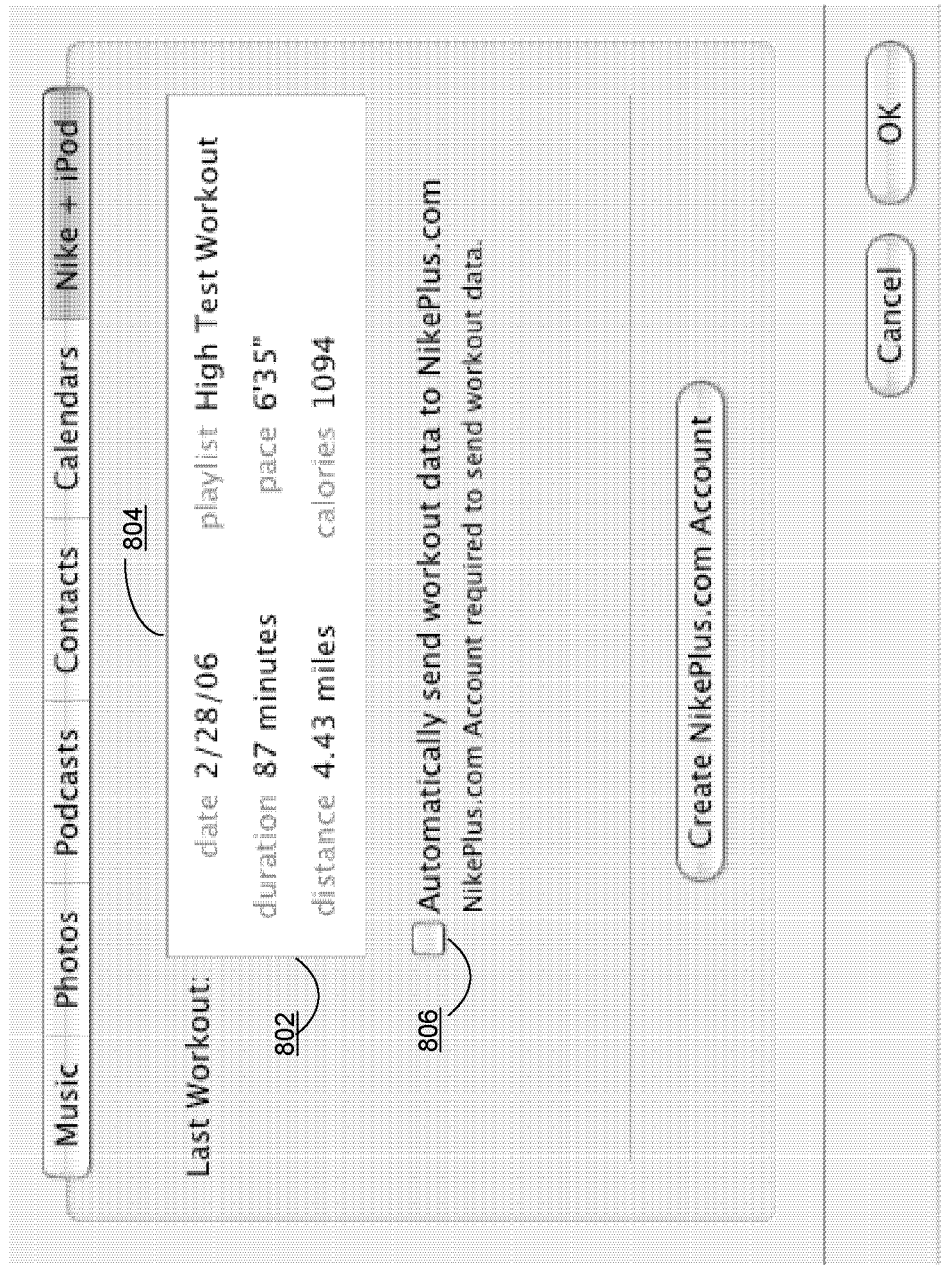
FIG. 8 illustrates a user interface screen, caused to be presented by processing within the host computer, to display an indication of some physiologic data.

As mentioned above, in some examples, physiologic data provided from a portable media player (such as the portable media player 104) to a workout data service (such as the workout data service 118) may be provided through a host computer (such as the host computer 116). FIG. 8 illustrates a user interface screen, caused to be presented by processing within the host computer, to display an indication of some of the physiologic data, namely, the physiologic information of the "last workout" in a portion 802 of the user interface screen. (This is just an example. An indication of other of the physiologic data may be displayed.) In addition to the information such as date, distance, pace and calories, the "last workout" information includes an indication 804 of the media play list associated with that workout. It is also of note that processing within the host computer 116 may also operate to automatically send the physiologic data to the workout data service 118 (e.g., accompanied by the access token discussed above, relative to FIG. S and the discussion of account set up with the workout data service 118), without ongoing user intervention. The user may control whether this automatic operation takes place via the check box 806 in the FIG. 8 user interface screen. This check box 806 would be initially unchecked if the user previously chose for physiologic data not to be sent at all to the workout data service 118, e.g. during initial setup (FIG. 4).

Figure 9:
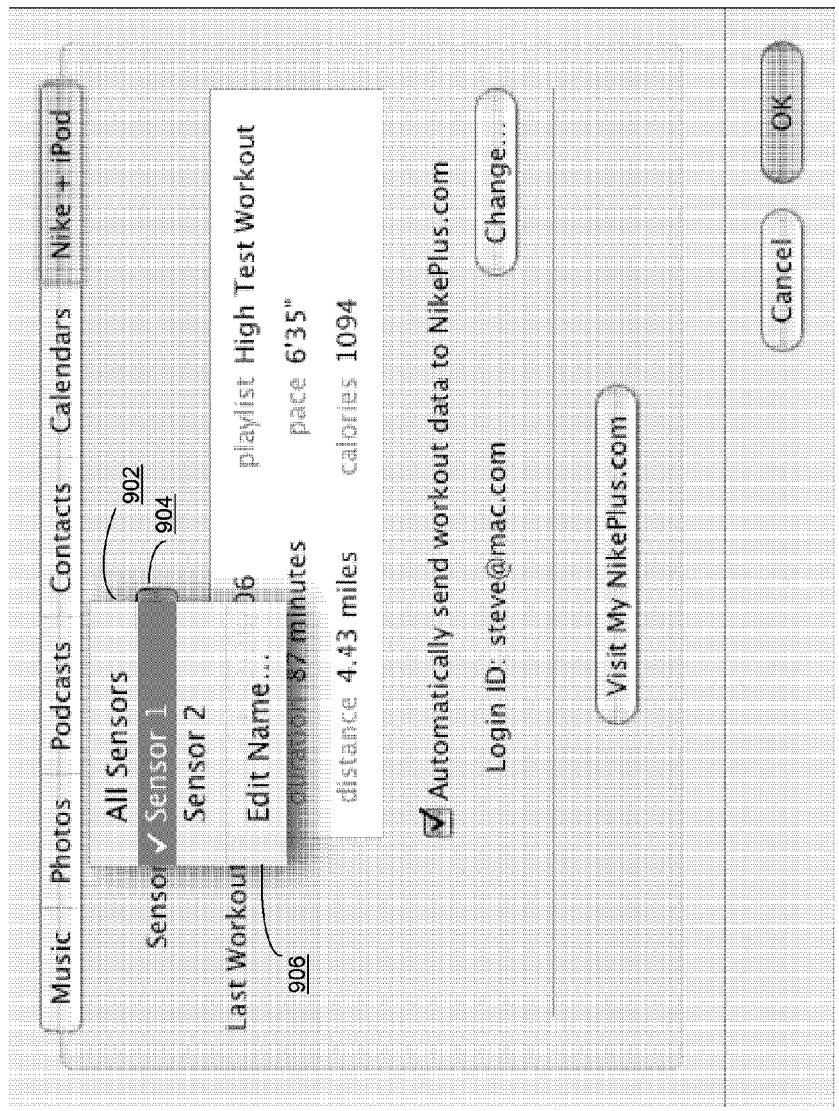
FIG. 9 illustrates a user interface screen, caused to be presented by processing within the host computer, to allow a user to choose between physiologic data gathering devices with which the portable media player has been paired.

While much of the previous description has described methods, applications and systems in the context of a single physiologic data gathering device, it has been mentioned above that there may be more than one physiologic data gathering device. FIG. 9 illustrates a user interface screen, caused to be presented by processing within the host computer, to allow a user to choose between physiologic data gathering devices with which the portable media player has been paired.

A menu item 902, in this case a pull down menu item, is provided to allow the user to choose which physiologic data gathering devices (listed as "sensors") for which data is to be considered and/or otherwise handled from within the application executing in the host computer. In FIG. 9, the "Sensor I" item 904 is checked. In addition, a user interface item 906 is provided to allow the user to edit the name ascribed to a particular physiologic data gathering device, relative to the application executing in the host computer.

In summary, then, we have described an overall architecture of a system, including a portable media player, generally usable for, among other things, monitoring and/or controlling user exercise or other activity or physiology. In addition, we have described how an application of a host computer, such as a media store application, operates in the context of such a system.

What is claimed is:

1. A method, comprising:
in a host computer, performing operations for:
  storing a workout playlist of songs for a workout template, the workout template comprising audio cues for a corresponding workout;
  processing the workout template, including playing songs in the workout playlist and playing the audio cues during the playing of the songs;
  while playing songs in the workout playlist and processing the workout template, receiving user input with respect to playback of songs from the workout playlist
  upon determining that the user input during playback of the songs from the playlist causes a different playback order than a pre-defined playback order in the workout playlist, suggesting, to a user, a modification to the workout playlist to correlate to the user input;
  based on receiving a first indication from the user of acceptance of the modification to the playlist, creating a modified playlist;
  suggesting, to the user, that the modified playlist should be stored as the workout playlist for the workout template;
  based on receiving a second indication from the user of acceptance of the suggestion, storing the modified playlist as the workout playlist for the workout template, so that songs in the modified playlist are played when subsequently processing the workout template; and
  based on physiologic data indicative of the user behavior, modifying the audio cues played during the playing of the songs.

2. The method of claim 1, wherein storing the modified playlist to the workout template comprises:

updating a corresponding entry in a workout identification table, the entry comprising a workout identification ("ID") and a playlist ID, wherein the workout ID indicates workout characteristics for a corresponding workout and the playlist ID indicates a playlist that defines media playback associated with the workout;

wherein the updating comprises updating the playlist ID with an identifier for the modified playlist.

3. The method of claim 2, wherein the entry in the workout identification table further comprises a template ID, the template ID indicating the audio cues for the corresponding workout.

4. The method of claim 1, wherein creating the modified playlist comprises:

in the host computer, performing operations for:

updating a corresponding entry in a playlist identification table with information about the modified playlist, the entry comprising a playlist ID and a listing of media in the playlist, wherein the playlist ID indicates a designation for the playlist;

wherein the updating comprises updating the playlist ID with an identifier for the modified playlist and updating the listing of media in the playlist to include media corresponding to the user behavior with respect to playback of the songs from the playlist.

5. The method of claim 4, wherein the entry in the playlist identification table with the information about the modified playlist comprises information associated with the playlist;

wherein the information associated with the playlist comprises a workout ID that indicates a workout during which the user played the songs of the playlist.

6. The method of claim 4, wherein the entry in the playlist identification table with the information about the modified playlist comprises information associated with the playlist;

wherein the information associated with the playlist is configured to store an identification of user behavior to override the modified playlist.

7. The method of claim 1, further comprising:

in the host computer, performing operations for:

determining that the modified playlist does not correspond to a preexisting playlist prior to suggesting, to the user, a correlation of the modified playlist with the workout template.

8. A host computer, comprising:

a processor; and a network interface;

the processor and network interface performing operations for:

storing a workout playlist of songs for a workout template, the workout template comprising audio cues for a corresponding workout;

processing the workout template, including playing songs in the workout playlist and playing the audio cues during the playing of the songs;

while playing songs in the workout playlist and processing the workout template, receiving user input with respect to playback of songs from the workout playlist;

upon determining that the user input during playback of the songs from the playlist causes a different playback order than a pre-defined playback order in the workout playlist, suggesting, to a user, a modification to the workout playlist to correlate to the user input;

based on receiving a first indication from the user of acceptance of the modification to the playlist, creating a modified playlist;

suggesting, to the user, that the modified playlist should be stored as the workout playlist for the workout template;

based on receiving a second indication from the user of acceptance of the suggestion, storing the modified playlist as the workout playlist for the workout template, so that songs in the modified playlist are played when subsequently processing the workout template; and based on physiologic data indicative of the user behavior, modifying the audio cues played during the playing of the songs.

9. The host computer of claim 8, wherein storing the modified playlist to the workout template comprises:

updating a corresponding entry in a workout identification table, the entry comprising a workout identification ("ID") and a playlist ID, wherein the workout ID indicates workout characteristics for a corresponding workout and the playlist ID indicates a playlist that defines media playback associated with the workout;

wherein the updating comprises updating the playlist ID with an identifier for the modified playlist.

10. The host computer of claim 9, wherein the entry in the workout identification table further comprises a template ID, the template ID indicating the audio cues for the corresponding workout.

11. The host computer of claim 8, wherein creating the modified playlist comprises:

updating a corresponding entry in a playlist identification table with information about the modified playlist, the entry comprising a playlist ID and a listing of media in the playlist, wherein the playlist ID indicates a designation for the playlist;

wherein the updating comprises updating the playlist ID with an identifier for the modified playlist and updating the listing of media in the playlist to include media corresponding to the user behavior with respect to playback of the songs from the playlist.

12. The host computer of claim 11, wherein the entry in the playlist identification table with the information about the modified playlist comprises information associated with the playlist;

wherein the information associated with the playlist comprises a workout ID that indicates a workout during which the user played the songs of the playlist.

13. The host computer of claim 11, wherein the entry in the playlist identification table with the information about the modified playlist comprises information associated with the playlist;

wherein the information associated with the playlist is configured to store an identification of user behavior to override the modified playlist.

14. The host computer of claim 8, further comprising:

the processor and network interface performing operations for:

determining that the modified playlist does not correspond to a preexisting playlist prior to suggesting, to the user, a correlation of the modified playlist with the workout template.

15. A non-transitory computer-readable storage medium storing instructions that, when executed by a host computer, cause the host computer to perform a method, the method comprising:

storing a workout playlist of songs for a workout template, the workout template comprising audio cues for a corresponding workout;

processing the workout template, including playing songs in the workout playlist and playing the audio cues during the playing of the songs;

while playing songs in the workout playlist and processing the workout template, receiving user input with respect to playback of songs from the workout playlist;

upon determining that the user input during playback of the songs from the playlist causes a different playback order than a pre-defined playback order in the workout playlist, suggesting, to a user, a modification to the workout playlist to correlate to: the user input;

based on receiving a first indication from the user of acceptance of the modification to the playlist, creating a modified playlist;

suggesting, to the user, that the modified playlist should be stored as the workout playlist for the workout template;

based on receiving a second indication from the user of acceptance of the suggestion, storing the modified playlist as the workout playlist for the workout template, so that songs in the modified playlist are played when subsequently processing the workout template; and based on physiologic data indicative of the user behavior, modifying the audio cues played during the playing of the songs.

16. The computer-readable storage medium of claim 15, wherein, storing the modified playlist to the workout template comprises:

updating a corresponding entry in a workout identification table, the entry comprising a workout identification ("ID") and a playlist ID, wherein the workout ID indicates workout characteristics for a corresponding workout and the playlist ID indicates a playlist that defines media playback associated with the workout;

wherein the updating comprises updating the playlist ID with an identifier for the modified playlist.

17. The computer-readable storage medium of claim 16, wherein the entry in the workout identification table further comprises a template ID, the template ID indicating the audio cues for the corresponding workout.

18. The computer-readable storage medium of claim 15, wherein creating the modified playlist comprises:

updating a corresponding entry in a playlist identification table with information about the modified playlist, the entry comprising a playlist ID and a listing of media in the playlist, wherein the playlist ID indicates a designation for the playlist;

wherein the updating comprises updating the playlist ID with an identifier for the modified playlist and updating the listing of media in the playlist to include media corresponding to the user behavior with respect to playback of the songs from the playlist.

19. The method of claim 1, wherein suggesting, to a user, a modification to the playlist to correlate to user behavior comprises:

suggesting a modification relating to a given song in the playlist based on user behavior during at least two instances of playback of the given song during corresponding processings of the workout template.

* * * * *